US011523776B2

(12) United States Patent  (10) Patent No.: US 11,523,776 B2
Kim et al.  (45) Date of Patent: Dec. 13, 2022

(54) BODY-ATTACHABLE BIOMETRIC SIGNAL ACQUISITION DEVICE

(71) Applicant: AI.MON Co., Ltd., Seoul (KR)

(72) Inventors: Jin Beom Kim, Yongin-si (KR); Sam Youl Park, Anyang-si (KR)

(73) Assignee: AI.MON CO., LTD., Seoul (KR)

( * ) Notice: Subject to any disclaimer, the term of this patent is extended or adjusted under 35 U.S.C. 154(b) by 375 days.

(21) Appl. No.: 16/715,858

(22) Filed: Dec. 16, 2019

(65) Prior Publication Data

US 2020/0187856 A1  Jun. 18, 2020

(30) Foreign Application Priority Data

Dec. 18, 2018 (KR) .......................... 10-2018-0163857

(51) Int. Cl.
 *A61B 5/00* (2006.01)
 *A61B 5/1455* (2006.01)
(52) U.S. Cl.
 CPC ........ *A61B 5/6802* (2013.01); *A61B 5/14551* (2013.01); *A61B 5/683* (2013.01); *A61B 5/6831* (2013.01); *A61B 5/6828* (2013.01); *A61B 2503/04* (2013.01); *A61B 2560/04* (2013.01)
(58) Field of Classification Search
 CPC .............. A61B 5/6802; A61B 5/14551; A61B 2503/04; A61B 2560/04; A61B 5/6828; A61B 5/683; A61B 5/01; A61B 5/024; A61B 5/14532; A61B 5/318; A61B 5/02055; A61B 5/6831; A61B 5/14552;
 (Continued)

(56) References Cited

U.S. PATENT DOCUMENTS 9,913,591 B2  3/2018 Lapetina et al.
2002/0025056 A1  2/2002 Fujita et al.
 (Continued)

FOREIGN PATENT DOCUMENTS

CN  106233363 A  12/2016
JP  2016-073338 A  5/2016
WO  WO-2014016761 A1 * 1/2014 ........... A61B 5/0022

*Primary Examiner* — Joseph M Dietrich
*Assistant Examiner* — Michael T. Holtzclaw
(74) *Attorney, Agent, or Firm* — Bridgeway IP Law Group, PLLC; Sang Ho Lee; Hyun Woo Shin

(57) ABSTRACT

Provided is a body-attachable biometric signal acquisition device. The body-attachable biometric signal acquisition device includes: a main body including a sensor acquiring a biometric signal in a state of closely adhering to a surface of a body; and a first fixing portion winding the body to fix the main body to the body, wherein the first fixing portion includes a first strap winding the body, the first strap includes a framework formed of an elastic material, and when the first strap winds the body to fasten the main body and the first fixing portion to the body, a pressure applied by the sensor to the surface of the body is generated by an elastic restoring moment generated by the framework, and a gap is present between a portion of an outer surface of the first strap, and the surface of the body, the portion being positioned between the framework and the surface of the body. An air cushion is provided to prevent wobbling of the main body caused by an excessive space formed due to body size variation.

34 Claims, 33 Drawing Sheets

(58) Field of Classification Search
CPC .... B32B 3/08; B32B 5/02; B32B 5/26; B32B 2535/00
See application file for complete search history.

(56) References Cited

U.S. PATENT DOCUMENTS

| | | | |
|---|---|---|---|
| 2002/0151775 A1* | 10/2002 | Kondo | G04G 21/025 600/344 |
| 2005/0234351 A1 | 10/2005 | Nishii et al. | |
| 2015/0157263 A1* | 6/2015 | Workman | A61B 5/11 600/595 |
| 2018/0055449 A1* | 3/2018 | Ko | A61B 5/318 |
| 2021/0219853 A1* | 7/2021 | Kohara | A61B 5/681 |

* cited by examiner

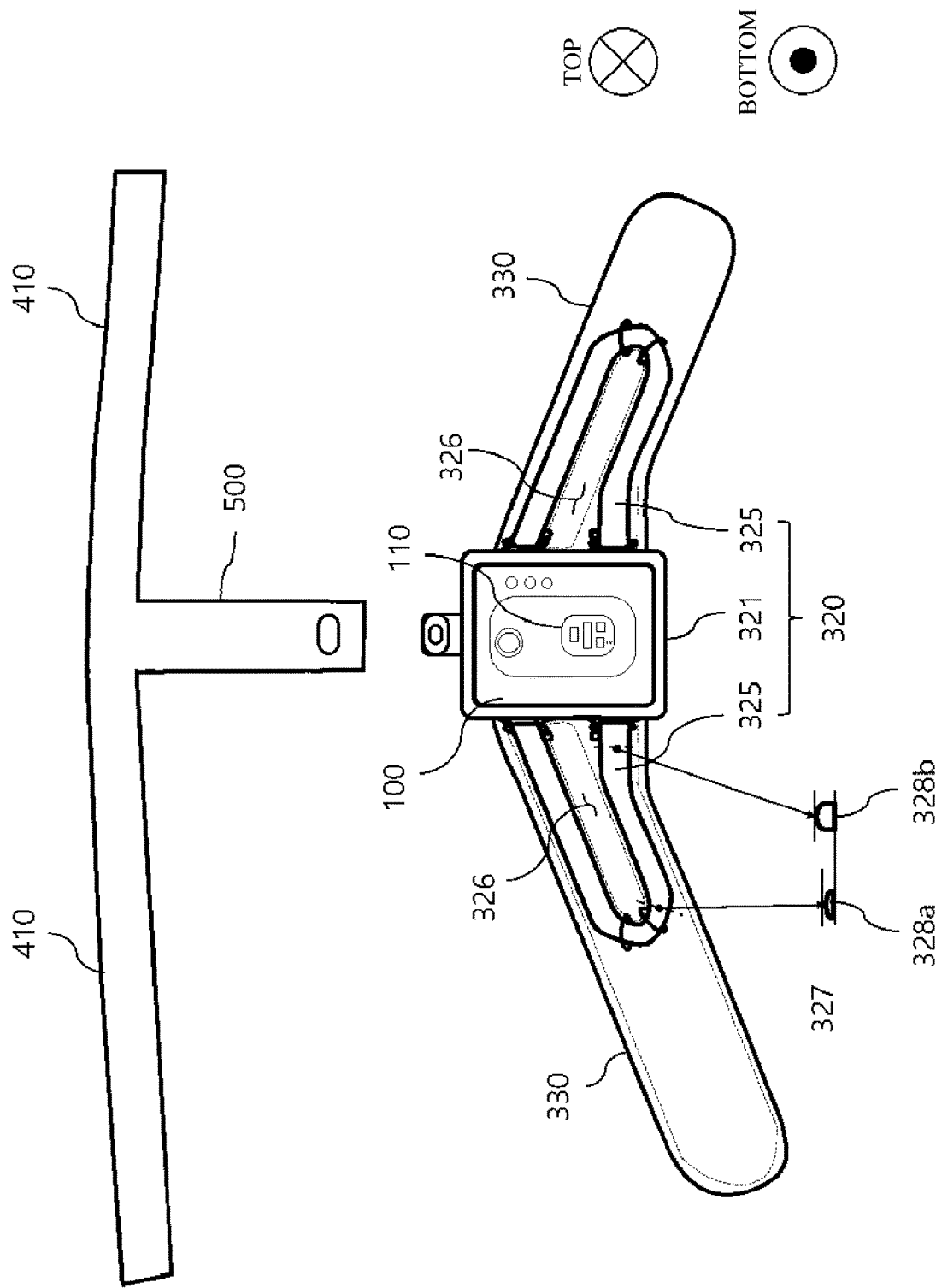

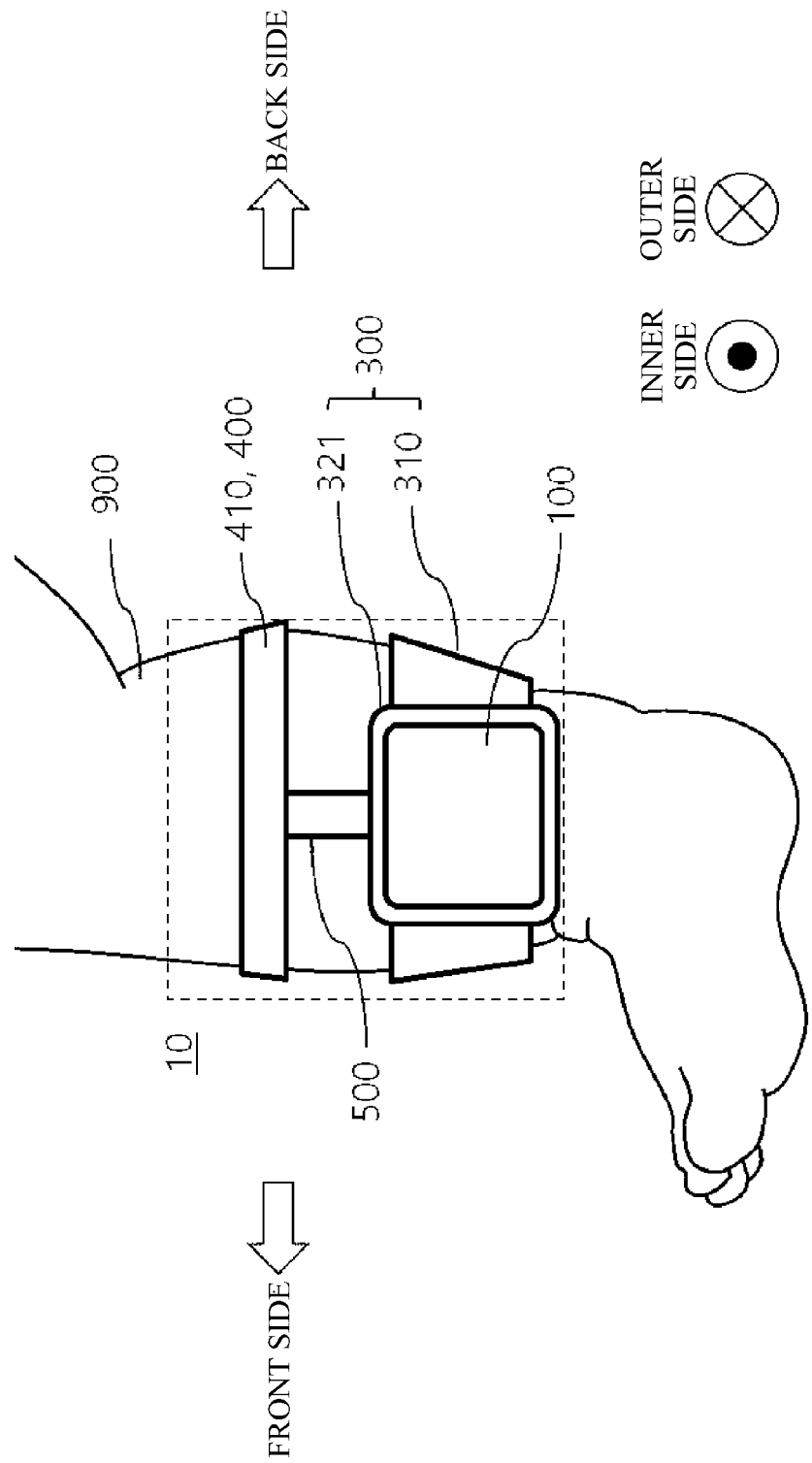

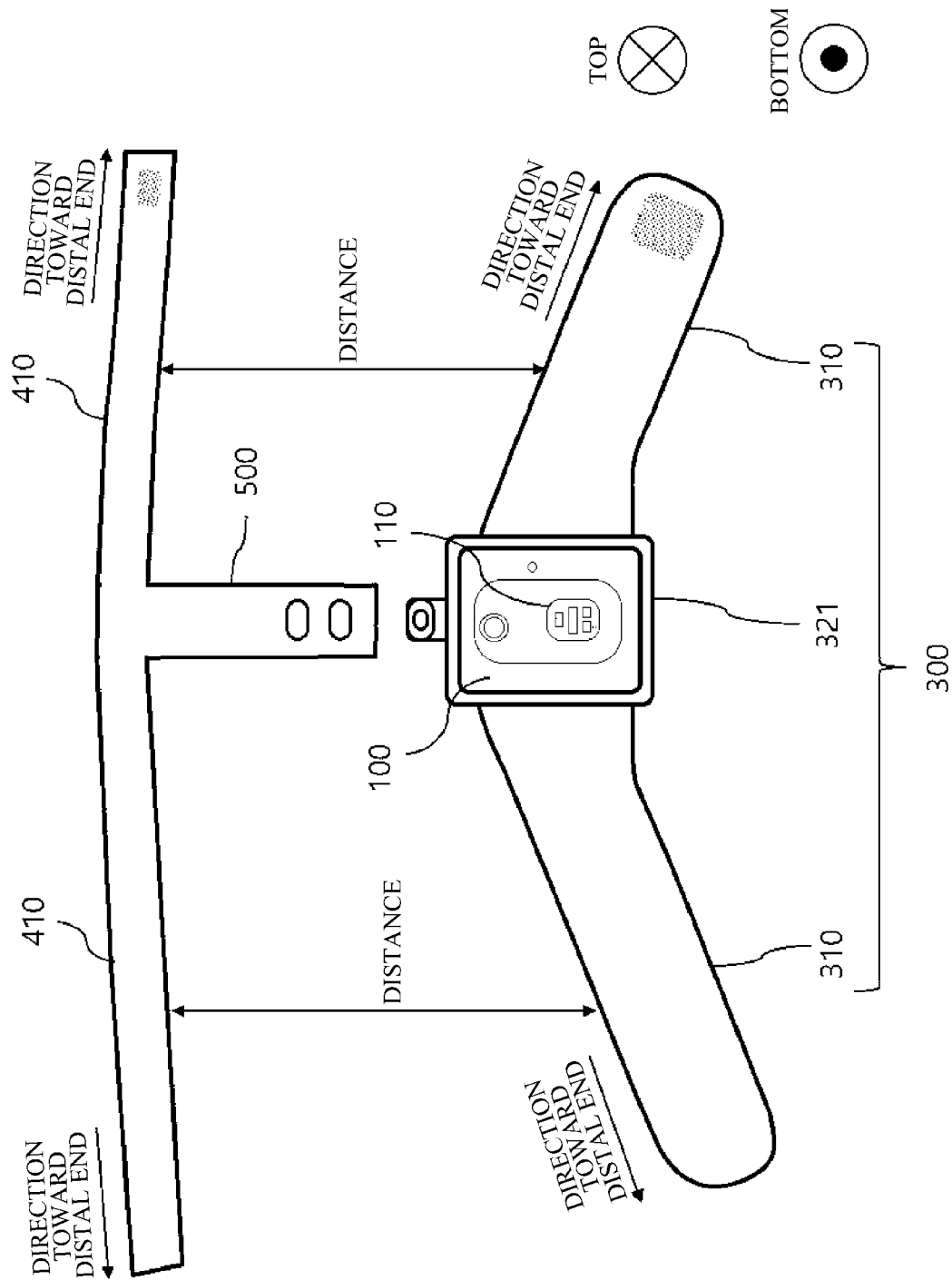

FIG. 16C
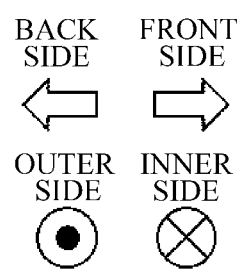
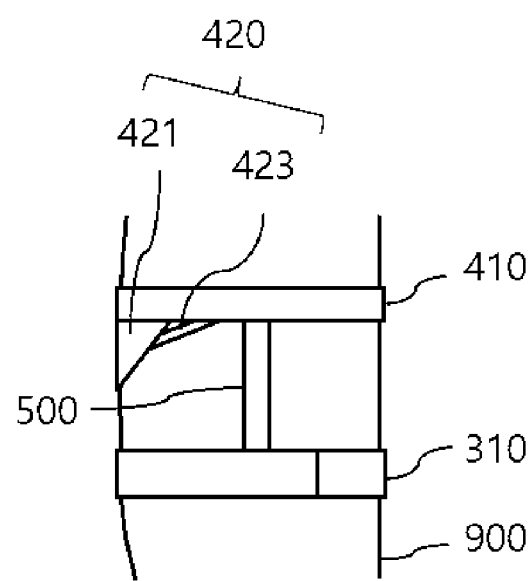

FIG. 17A
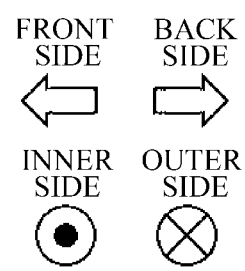
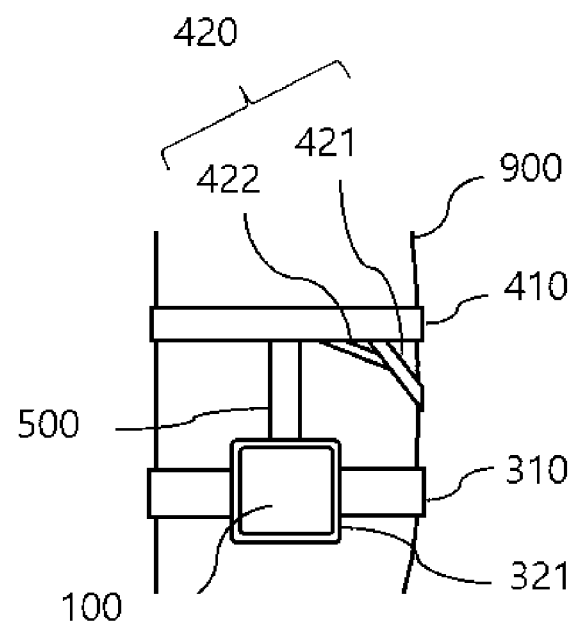

FIG. 17C
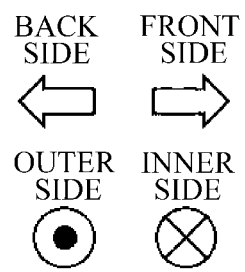
BACK SIDE ⇐   FRONT SIDE ⇒
OUTER SIDE ⊙   INNER SIDE ⊗
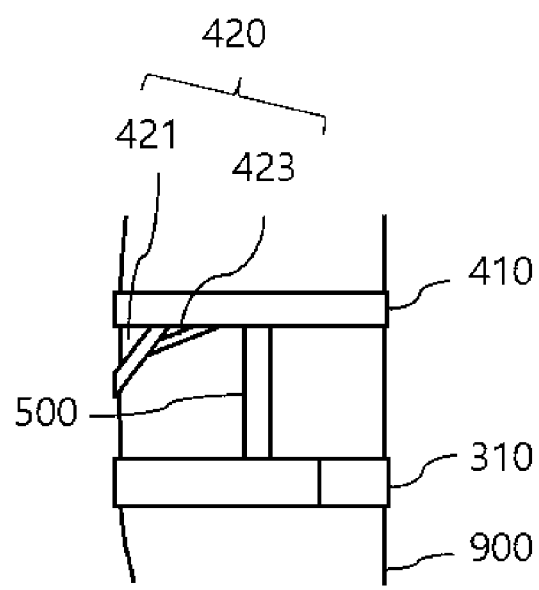

FIG. 18C
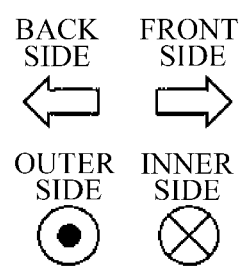
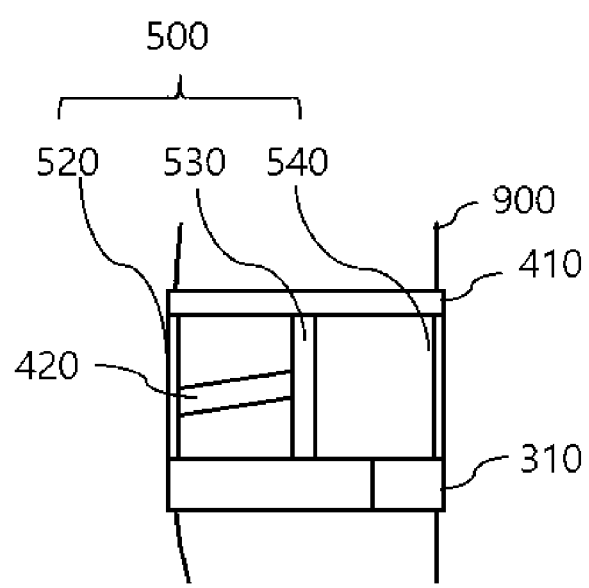

FIG. 19C
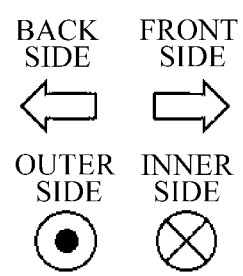
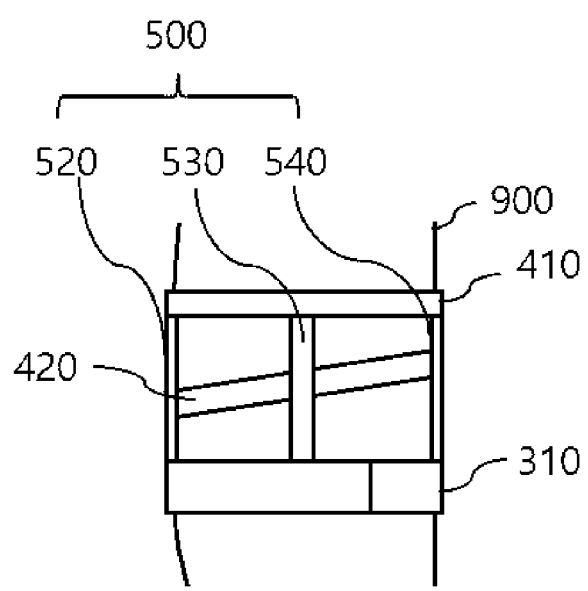

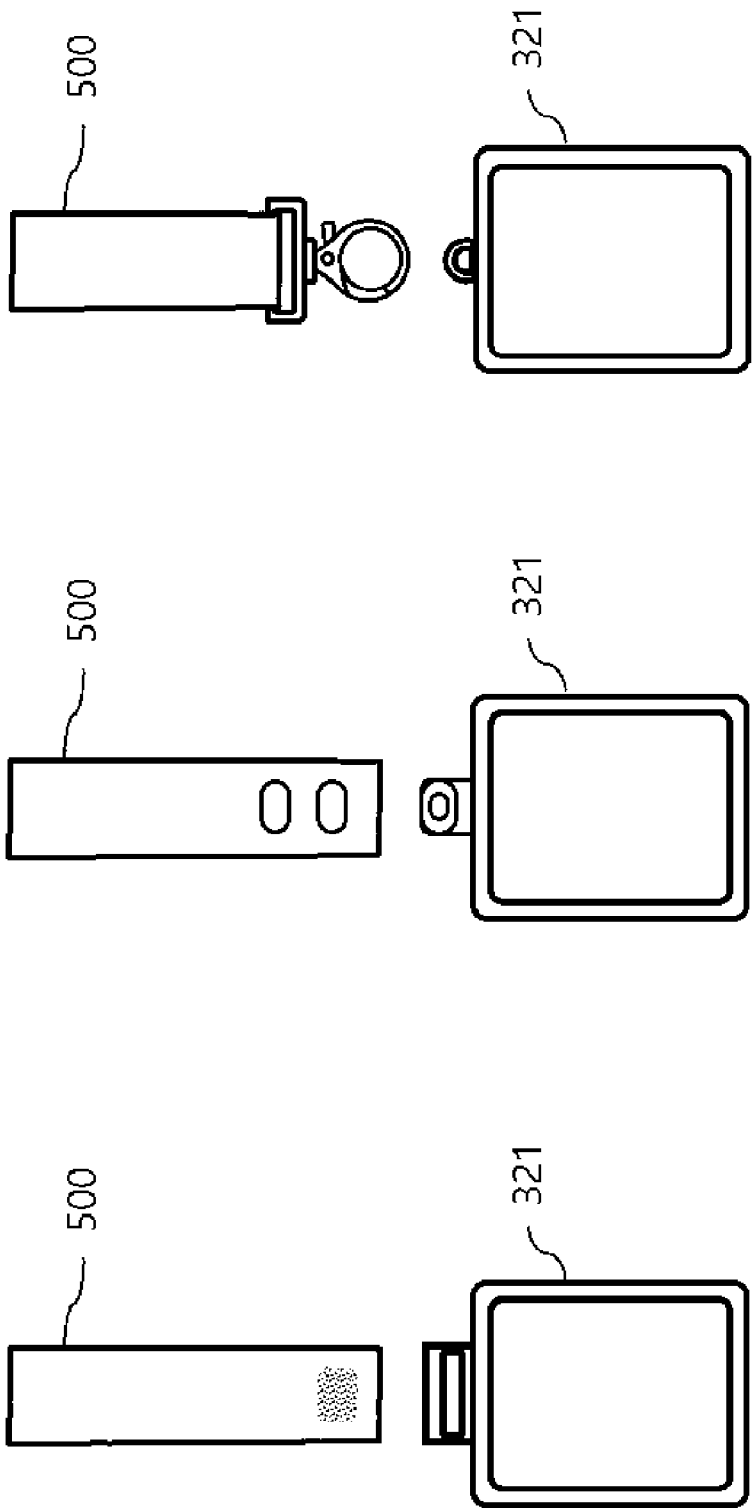

BODY-ATTACHABLE BIOMETRIC SIGNAL ACQUISITION DEVICE

CROSS-REFERENCE TO RELATED APPLICATION

This application claims the priority and benefit of Korean Patent Application No. 10-2018-0163857 filed on Dec. 18, 2018, with the Korean Intellectual Property Office, the disclosure of which is incorporated herein by reference.

BACKGROUND OF THE INVENTION

1. Field of the Invention

The present invention relates to a body-attachable biometric signal acquisition device, and more particularly, to a biometric signal acquisition device that may be attached to a body and acquire a high quality biometric signal.

2. Description of the Related Art

A protector of an infant or a patient desires to detect and treat a medical emergency early. However, it is required to continuously monitor a biometric signal such as an oxygen saturation level to detect the medical emergency early. The monitoring of the biometric signal may be implemented by using a medical instrument including a biometric signal sensor. However, since such a medical instrument is expensive and massive, it is difficult to use it in a general domestic environment other than a hospital.

Therefore, there is a demand for a biometric signal acquisition device attached to a body of an infant or a patient to notify a protector when an abnormal condition occurs, such that the protector may rapidly take an emergency measure. Such a biometric signal acquisition device may be used in a general domestic environment, instead of directly monitoring the infant or the patient. In particular, a death caused by an emergency condition, such as sudden infant death syndrome, needs to be prevented by measuring an important biometric signal related to respiration, such as a pulse rate and an oxygen saturation level.

Recently, biometric signal sensors such as a photoplethysmography (PPG) sensor which may measure an oxygen saturation level have been miniaturized and produced for a low price. Further, with the development of a wireless communication technology such as Bluetooth, a terminal device such as a smartphone, a smartband, or a smartwatch has a biometric signal acquisition function. However, such a terminal device is not suitable for monitoring an emergency condition of an infant or a patient.

This is because such a terminal device has a limitation that it is difficult for a sensor to continuously and stably contact a skin to maintain close adherence while preventing the sensor from slipping down on the body, and skin health and hygiene are not considered.

In a case where the sensor may not closely adhere to the skin, problems such as light leakage and a motion artifact occurs. Particularly, in a case where light leakage occurs, a biometric signal may not be normally acquired, and may be distorted. In order to prevent such a problem, a method of allowing the sensor to firmly adhere to the skin by, for example, tightening body fixing means such as a strap may be considered. In this case, however, delicate skin may become congested with blood, or the like, which is problematic. Therefore, there is a demand for a structure that may implement reliability in biometric signal acquisition, and skin health, simultaneously, by maintaining an adequate pressure to allow the sensor and the skin closely adhere to each other even in a case where a size of the body varies.

The strap is formed of a soft material such as a fabric to significantly reduce skin irritation and maintain skin health even when the body moves. However, in a case of producing the strap only by using the fabric material, although the sensor may adhere to the body by attaching Velcro, it is difficult to generate an elastic restoring moment, and thus the strap needs to be firmly tightened for close adherence of the sensor, which is disadvantageous.

In addition, in a case of using a soft silicone material or the like, Velcro may not be easily attached to the silicone material, such that it is difficult to fasten the terminal device while maintaining close adherence of the sensor to the body.

A gap is formed between the strap and the body when the elastic restoring moment is generated, and since infants grow fast, a body size and a body shape greatly vary between individuals and at difference ages. Therefore, wobbling of the terminal device may occur.

SUMMARY OF THE INVENTION

An object of the present invention is to provide a body-attachable biometric signal acquisition device that overcomes a problem caused by a difference in a body shape and a body size and thus may stably acquire a biometric signal by continuously adhering to a body.

Another object of the present invention is to provide a body-attachable biometric acquisition device capable of being easily fastened to a body, and maintaining a fixed state without being separated from or slipping on the body even when the body frequently moves.

Another object of the present invention is to provide a biometric signal acquisition device in which a main body may be supported with an adequate force in a case where the main body is fixed to the body.

Another object of the present invention is to provide a body-attachable biometric signal acquisition device capable of significantly reducing skin irritation by using a strap formed of a body-friendly material to stably acquire a biometric signal while maintaining skin health and hygiene even during prolonged wearing.

According to an exemplary embodiment of the present invention, a body-attachable biometric signal acquisition device includes: a main body including a sensor acquiring a biometric signal in a state of closely adhering to a surface of a body; and a first fixing portion winding the body to fix the main body to the body, wherein the first fixing portion includes a first strap winding the body, the first strap includes a framework formed of an elastic material, and when the first strap winds the body to fasten the main body and the first fixing portion to the body, a pressure applied by the sensor to the surface of the body is generated by an elastic restoring moment generated by the framework, and a gap is present between a portion of an outer surface of the first strap, and the surface of the body, the portion being positioned between the framework and the surface of the body.

The framework may include a main body support portion formed to surround a side surface of the main body to support the main body when the main body is engaged with the first fixing portion; and elastic restoring moment generating portions attached to or formed integrally with the main body support portion and generating the elastic restoring moment.

The elastic restoring moment generating portions may extend from opposite outer side surfaces of the main body support portion, respectively, and may be attached to or formed integrally with the opposite outer side surfaces, respectively.

The elastic restoring moment generating portions may each have a distal end separated from the surface of the body when the sensor is brought into contact with an attaching portion of the body, and the elastic restoring moment generating portions may each have one end connected to the main body support portion, the one end having a cross section which is taken in a direction perpendicular to a length direction of the elastic restoring moment generating portion and of which a thickness and an area are larger than those of a cross section of the distal end.

The main body support portion may be separable from the main body, a hole may be formed in the main body support portion in a direction away from the surface of the body so that the main body is engageable with the main body support portion, the hole may have one opening facing the body and having an area larger than that of the other opening, and a groove to which the main body support portion is fixed may be formed along the side surface of the main body.

The body-attachable biometric signal acquisition device may further include: a ring fused to an inner surface of the first hole along the inner surface of the hole, and formed of a material having a hardness higher than that of a material of the main body support portion.

The sensor may be formed on a lower surface of the main body, and roundings may be formed at corners of the main body and the main body support portion that face the body.

The main body support portion may include a top cover supporting an upper portion of the main body to prevent the main body from being separated.

The main body support portion may be separable from the main body, a hole may be formed in the main body support portion in a direction away from the surface of the body so that the main body is engageable with the main body support portion, and a rugged portion supporting the pressure generated between the sensor and the surface of the body may be formed on a surface of the hole with which the main body is engaged.

The rugged portion may have a curved cross section.

The rugged portion may have an S-letter shaped cross section.

The main body support portion may include a support supporting a lower portion of the main body to prevent the main body from slipping on the surface of the body.

The main body support portion may have any one of a rectangular shape, a square shape, a circular shape, or an oval shape, when viewed from above.

An entire length of the framework may be half or more than half of a circumference of a portion of the body on which the first fixing portion winds, the first fixing portion may include fasteners formed at opposite distal ends of the first fixing portion, respectively, and fastened to each other, and a fastening position or a fastening area of the fasteners may be adjustable according to a size variation of the body.

The elastic restoring moment generating portions may extend from the opposite outer side surfaces of the main body support portion, respectively, and be attached to or formed integrally with the opposite outer side surfaces, respectively, the elastic restoring moment generating portions may each have a distal end separated from the surface of the body when the sensor is brought into contact with an attaching portion of the body, and the elastic restoring moment generating portion may include a first elastic material member connected to the main body support portion, and a second elastic material member fused to or adhering to the first elastic material member and having a hardness lower than that of the first elastic material member by a predetermined value.

The first strap may include two straps extending from the opposite outer side surfaces of the main body support portion, the first fixing portion may include at least one air cushion each having an opened or closed cavity therein, the at least one air cushion may each be formed on a surface of each of the two straps at a position close to the main body when the first strap winds the body to fasten the main body and the first fixing portion to the body, the surface of each of the two straps being a surface facing the body, the air cushion may support the surface of the body to prevent the main body from wobbling when the first strap winds the body to fasten the main body and the first fixing portion to the body, and each of the two straps may include the framework formed of the elastic material, and an outer cover enclosing the framework or part of the framework, or fused to the framework, and formed of a fabric material or an elastic material.

The air cushion may be formed integrally with or attached to the framework, and a volume of the cavity in the air cushion may be decreased as the pressure is increased.

The air cushion may include at least one arc-shaped member including at least one hole formed in a direction perpendicular to a direction in which the outer cover extends from each of the opposite outer side surfaces of the main body support portion.

The number of holes formed in the arc-shaped member may be plural.

The air cushion may be formed of a fabric material and formed on a surface of each outer cover at a position close to the main body, the surface of each outer cover being a surface facing the body when the first strap winds the body to fasten the main body and the first fixing portion to the body.

The air cushion may include at least one arc-shaped member including at least one hole formed in a direction perpendicular to a direction in which the outer cover extends from each of the opposite outer side surfaces of the main body support portion.

The outer cover may be fused to the elastic restoring moment generating portion and formed of the elastic material having a hardness lower than that of the elastic restoring moment generating portion, and the air cushion may be formed on a surface of each outer cover at a position close to the main body, the surface of each outer cover being a surface facing the body when the first strap winds the body to fasten the main body and the first fixing portion to the body.

The air cushion may include at least one arc-shaped member including at least one hole formed in a direction perpendicular to a direction in which the outer cover extends from each of the opposite outer side surfaces of the main body support portion.

The number of holes formed in the arc-shaped member may be plural.

The outer cover may be formed of the fabric material, may be connected to the elastic restoring moment generating portion and the air cushion with Velcro, and may enclose the elastic restoring moment generating portion and the air cushion.

Opposite sides of the elastic restoring moment generating portion may each have a ring shape with an empty middle portion, and the outer cover may be sewed along an inner boundary of the ring shape.

Linings positioned at one surface of the outer cover, and outer shells positioned at another surface opposite to the one surface may be formed of one or more layers of fabric material, the one surface facing the surface of the body when the first fixing portion winds the body to fasten the main body to the body, and the elastic restoring moment generating portion may adhere or be fused between the linings and the outer shells.

The linings may be formed of a material softer than that of the outer shells, the outer shells may be formed of a material that is more easily attachable with Velcro than that of the linings is, and the linings and the outer shells may adhere or be fused to the elastic restoring moment generating portion by using an adhesive, an adhesion film, or a synthetic resin material.

The elastic restoring moment generating portion may include one or more sewing holes for sewing and be sewed to the outer cover through the sewing holes.

The outer cover may be fused to a surface or part of the surface of the elastic restoring moment generating portion, the surface being a surface facing the body when the first fixing portion winds the body to fasten the main body to the body, the outer cover may be formed of the elastic material having a hardness lower than that of the elastic restoring moment generating portion, and the outer cover and the elastic restoring moment generating portion may be fused to each other while forming an inclined surface at a predetermined angle.

When viewed from a side of the first fixing portion, the outer cover and the elastic restoring moment generating portion may be fused in a diagonal line shape, a V-letter shape, or a saw-tooth shape.

The outer cover may be fused to a surface or part of the surface of the elastic restoring moment generating portion, the surface being opposite to the surface facing the body.

The frameworks may be formed to be spaced apart from opposite outer side surfaces of the main body by a predetermined distance, respectively, and extend from the opposite outer side surfaces of the main body, respectively.

The frameworks may each have a distal end separated from the surface of the body when the sensor is brought into contact with an attaching portion of the body, and the frameworks may each have one end connected to a main body support portion, the one end having a cross section which is taken in a direction perpendicular to a length direction of the framework and of which a thickness and an area are larger than those of a cross section of the distal end.

A protruding portion may be formed at each of the opposite outer side surfaces of the main body, and a slot to which the first strap is detachably attached may be formed at a distal end of the protruding portion.

The body-attachable biometric signal acquisition device may further include outer covers each fused to a surface or part of the surface of the framework, the surface being opposite to the surface facing the body.

The frameworks may each have a distal end separated from the surface of the body when the sensor is brought into contact with an attaching portion of the body, and the frameworks may each include a first elastic material member, and a second elastic material member fused to a distal end of the first elastic material member in a length direction and having a hardness lower than that of the first elastic material member by a predetermined value.

The body-attachable biometric signal acquisition device may further include air cushions each having a cavity therein or padded, and formed on end portions of the opposite outer side surfaces of the main body, the end portions facing the body, wherein the air cushion supports the surface of the body to prevent the main body from wobbling when the first strap winds the body to fasten the main body and the first fixing portion to the body, and the air cushion includes at least one arc-shaped member including at least one hole formed in a direction perpendicular to a direction in which the outer cover extends from each of the opposite outer side surfaces of the main body support portion.

The body-attachable biometric signal acquisition device may further include outer covers formed of an elastic material having a hardness lower than that of the material of the framework, wherein the outer cover is fused to a surface or part of the surface of the framework, the surface being a surface facing the body when the first fixing portion winds the body to fasten the main body to the body, and the outer cover encloses the framework, or the outer cover and the framework are fused to each other while forming an inclined surface at a predetermined angle.

When viewed from a side of the first fixing portion, the outer cover and the framework may be fused in a diagonal line shape, a V-letter shape, or a saw-tooth shape.

The outer cover may be fused to a surface or part of the surface of the framework, the surface being opposite to the surface facing the body.

BRIEF DESCRIPTION OF THE DRAWINGS

FIG. 8 is a view illustrating a body-attachable biometric signal acquisition device according to an exemplary embodiment of the present invention;

FIG. 13 is a view illustrating a state in which a body-attachable biometric signal acquisition device is attached to a body, according to an exemplary embodiment of the present invention;

FIG. 14 is a view illustrating a body-attachable biometric signal acquisition device according to an exemplary embodiment of the present invention;

FIGS. 16A to 16C are views each illustrating a state in which a body-attachable biometric signal acquisition device is attached to a body, according to an exemplary embodiment of the present invention;

FIGS. 17A to 17C are views each illustrating a state in which a body-attachable biometric signal acquisition device is attached to a body, according to an exemplary embodiment of the present invention;

FIGS. 18A to 18C are views each illustrating a state in which a body-attachable biometric signal acquisition device is attached to a body, according to an exemplary embodiment of the present invention;

FIGS. 19A to 19C are views each illustrating a state in which a body-attachable biometric signal acquisition device is attached to a body, according to an exemplary embodiment of the present invention;

FIG. 22 is a view illustrating forms in which a first fixing portion and a first connection portion of a body-attachable biometric signal acquisition device are fastened to each other, according to an exemplary embodiment of the present invention.

DETAILED DESCRIPTION

The above-mentioned objects, features, and advantages will become more obvious from the following detailed description provided in relation to the accompanying drawings. Therefore, those skilled in the art to which the present invention pertains may easily practice a technical idea of the present invention.

Further, it is to be understood that all detailed descriptions mentioning specific exemplary embodiments of the present invention as well as principles, aspects, and exemplary embodiments of the present invention are intended to include structural and functional equivalences thereof. Further, it is to be understood that these equivalences include an equivalence that will be developed in the future as well as an equivalence that is currently well-known, that is, all elements invented so as to perform the same function regardless of a structure. Further, in describing the present invention, in the case in which it is decided that a detailed description of a well-known technology associated with the present invention may unnecessarily make the gist of the present invention unclear, it will be omitted.

Hereinafter, various exemplary embodiments of the present invention will be described in detail with reference to the accompanying drawings.

A body-attachable biometric signal acquisition device 10 according to the present invention is a device attachable to a body 900 of a human.

Figure 1:
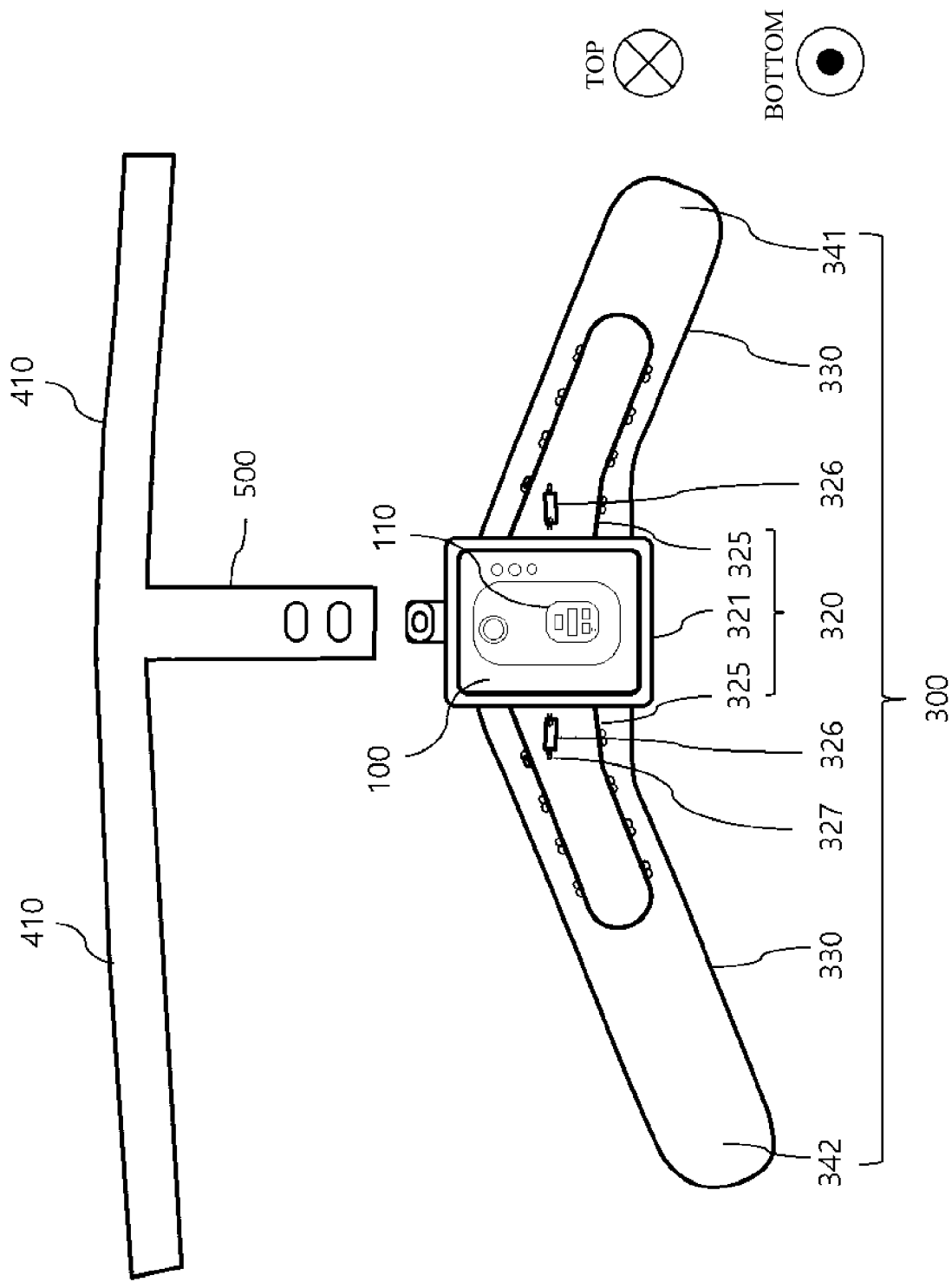
FIG. 1 is a view illustrating a body-attachable biometric signal acquisition device according to an exemplary embodiment of the present invention.

FIG. 1 is a view illustrating a body-attachable biometric signal acquisition device according to an exemplary embodiment of the present invention. As illustrated in FIG. 1, the biometric signal acquisition device 10 that is attachable to the body 900 according to an exemplary embodiment of the present invention may include: a main body 100 including a sensor 110 acquiring a biometric signal in a state of closely adhering to a surface of the body 900; and a first fixing portion 300 which winds the body 900 to fix the main body 100 and to which the main body 100 is detachably attached, in which the first fixing portion 300 may include a framework 320 formed of an elastic material, and outer covers 330 entirely or partially enclosing the framework 320 or fused to the framework 320. In FIG. 1, a bottom portion of the outer cover 330 coming into contact with the surface of the body 900 is omitted.

The biometric signal may include one or more of an oxygen saturation level, a pulse rate, an electrocardiogram, a body temperature, a blood sugar level, and a secretion.

In particular, in a case where the biometric signal is an oxygen saturation level, the sensor 110 may be a module (photoplethysmography (PPG) sensor) including a photodiode and a light emitting diode. A proportion of oxyhemoglobin may be obtained by measuring current values obtained by transmitting or reflecting infrared light or a red light signal with respect to skin and calculating a ratio of the current values of the infrared light and the red light signal, and the oxygen saturation level may be acquired by using the proportion of oxyhemoglobin. To this end, the sensor 110 is positioned on a bottom portion (a surface facing the surface of the body 900 when being attached to the body 900) of the main body 100. It is preferable that the sensor 110 protrudes from the surface of the main body 100 so as to closely adhere to the surface of the body 900. Such a structure in which the sensor 110 protrudes enables close adherence of the sensor even in a case where a body size varies.

An elastic material used to form the framework 320 is preferably a thermoplastic elastomer (TPE) or a synthetic resin (plastic). The framework 320 may be deformed by an external force due to an elastic force of the elastic material, but may be restored to an original state once the external force is removed. The framework 320 has a hardness higher than that of the outer cover 330 and needs to function as a shape-maintaining framework. However, the elastic material may not necessarily be constituted by one material, but may have a form in which a plurality of materials having hardnesses different from each other are bonded to each other.

Figure 2:
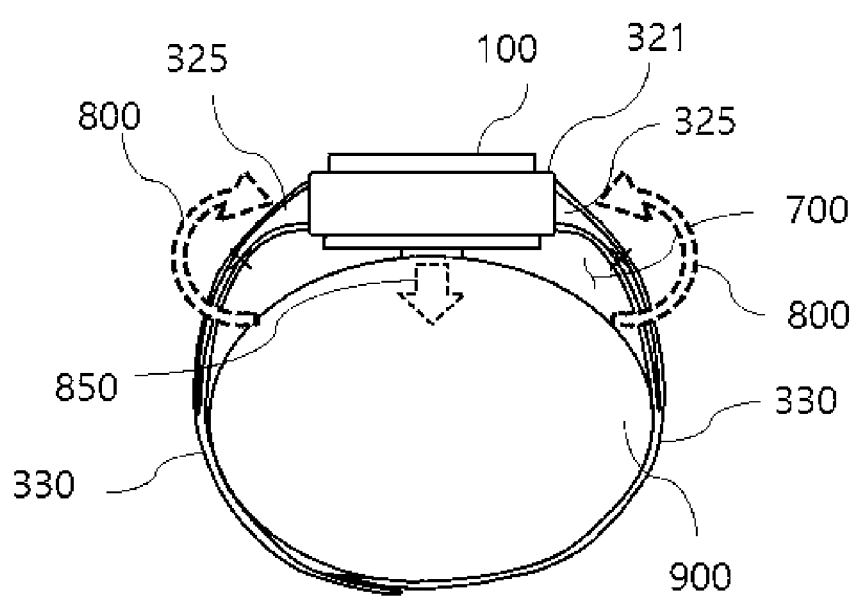
FIG. 2 is a view illustrating a state in which the body-attachable biometric signal acquisition device is attached to a body, according to an exemplary embodiment of the present invention.

FIG. 2 is a view illustrating a state in which the body-attachable biometric signal acquisition device is attached to a body, according to an exemplary embodiment of the present invention. As illustrated in FIG. 2, in a case where the first fixing portion 300 winds the body 900 to fix the main body 100 to the body 900, a pressure applied by the sensor 110 to the surface of the body 900 may be generated by an elastic restoring moment 800 generated by the framework 320.

More specifically, the biometric signal acquisition device 10 that is attachable to a body according to the present invention may include: the main body 100 including the sensor 110 acquiring a biometric signal in a state of closely adhering to the surface of the body 900; and the first fixing portion 300 winding the body 900 to fix the main body 100 to the body 900, in which the first fixing portion 300 may include a first strap 310 that may wind the body 900, the first strap 310 may include the framework 320 formed of the elastic material, and when the first strap 310 winds the body 900 to fasten the main body 100 and the first fixing portion 300 to the body 900, a pressure 850 applied by the sensor to the surface of the body is generated by the elastic restoring moment 800 generated by the framework 320, and a gap 700 may be present between a portion of an outer surface of the first strap 310, and the surface of the body 900, the portion being positioned between the framework 320 and the surface of the body 900.

A moment refers to application of a force to rotate an object. In the present invention, the elastic restoring moment 800 refers to a moment generated in a direction to restore a deformed elastic cantilever in reaction to application of an external force to one distal end of the cantilever in a direction perpendicular to a length direction of the cantilever.

In a case where the first fixing portion 300 winds the body 900 to fasten the main body 100 to the body 900 in a state in which elastic restoring moment generating portions 325 are provided, an effect similar to drawing a bow may be exhibited. In this case, a bottom surface of the main body 100 may continuously and closely adhere to the surface of the body 900 to prevent light leakage, such that it is possible to maintain measurement performance of the sensor 110.

Further, as illustrated in FIG. 1, the framework 320 may include: a main body support portion 321 formed to surround a side surface of the main body 100 to support the main body 100 when the main body 100 is engaged with the first fixing portion 300; and the elastic restoring moment generating portions 325 attached to or formed integrally with the main body support portion 321 and generating the elastic restoring moment 800.

Further, it is preferable that the elastic restoring moment generating portions 325 each extend in a U-letter shape from each of opposite outer side surfaces of the main body support portion 321, and are attached to or formed integrally with the opposite outer side surfaces.

Figure 3:
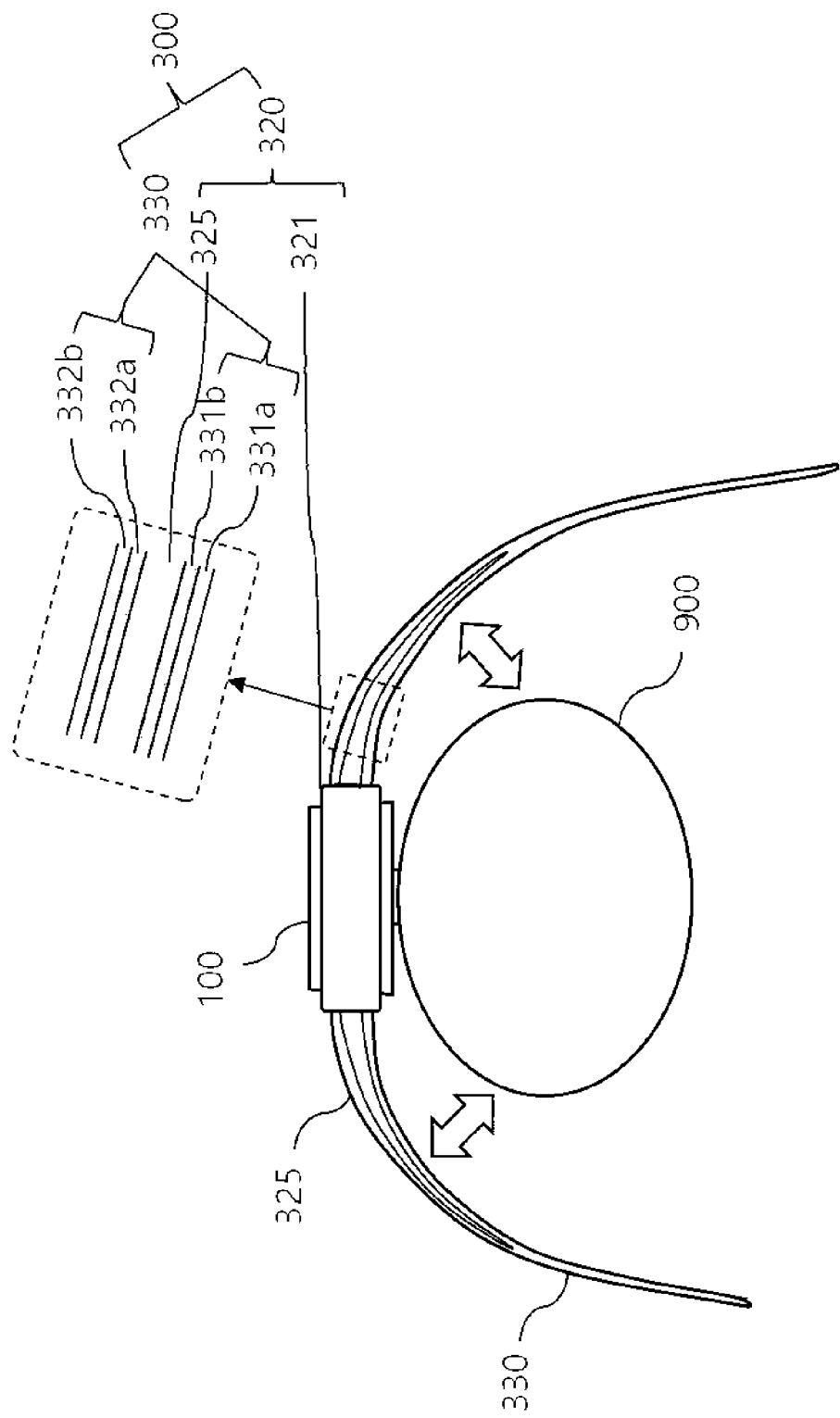
FIG. 3 is a view illustrating the body-attachable biometric signal acquisition device according to an exemplary embodiment of the present invention.

FIG. 3 is a view illustrating the body-attachable biometric signal acquisition device according to an exemplary embodiment of the present invention. FIG. 3 illustrates cross sections of the elastic restoring moment generating portion 325 and the outer cover 330 in a length direction.

As illustrated in FIG. 3, the elastic restoring moment generating portions 325 each have a distal end separated from the surface of the body 900 when the sensor 110 is brought into contact with an attaching portion of the body 900. It is preferable that the elastic restoring moment generating portions 325 each have one end connected to the main body support portion 321, the one end having a cross section 328b which is taken in a direction perpendicular to a length direction of the elastic restoring moment generating portion 325 and of which a thickness and an area are larger than those of a cross section 328a of the distal end.

As the area of the cross section of the elastic restoring moment generating portion 325 varies in the length direction, the gap 700 may be formed between the outer cover 330 and the surface of the body 900 at a position close to the main body support portion 321, and the outer cover 330 may closely adhere to the surface of the body 900 at a position distant from the main body support portion 321.

It is preferable that the thickness of the cross section of each of the one ends of the elastic restoring moment generating portion 325 is one or more times larger than that of the cross section of each of the distal ends of the elastic restoring moment generating portion 325.

Meanwhile, the elastic restoring moment generating portions 325 extend from the opposite outer side surfaces of the main body support portion 321, respectively, and are attached to or formed integrally with the opposite outer side surfaces, respectively. The elastic restoring moment generating portions 325 each have the distal end separated from the surface of the body 900 when the sensor 110 is brought into contact with the attaching portion of the body 900. The elastic restoring moment generating portion 325 may include a first elastic material member connected to the main body support portion 321, and a second elastic material member fused to or adhering to the first elastic material member and having a hardness lower than that of the first elastic material member by a predetermined value.

According to an exemplary embodiment of the present invention, the predetermined value is preferably 1 or more.

An entire length of the framework 320 is half or more than half of a circumference of a portion of the body 900 on which the first fixing portion 300 winds. The first fixing portion 300 includes fasteners 341 and 342 formed at opposite distal ends of the first fixing portion 300, respectively, and fastened to each other, and it is preferable that a fastening position or a fastening area of the fasteners 341 and 342 may be adjusted according to size variation of the body 900.

In general, when a watch is worn or a belt is tied, a force is applied in a direction to press the body to fasten fasteners to each other. In this case, however, skin may be damaged in a case where the body 900 is a delicate body of an infant. Therefore, in the exemplary embodiment of the present invention, the fasteners 341 and 342 are fastened to each other in a state in which the gap 700 is formed, such that it is possible to prevent the damage to the skin of the body 900 caused by the pressure applied by the fasteners.

Figure 4:
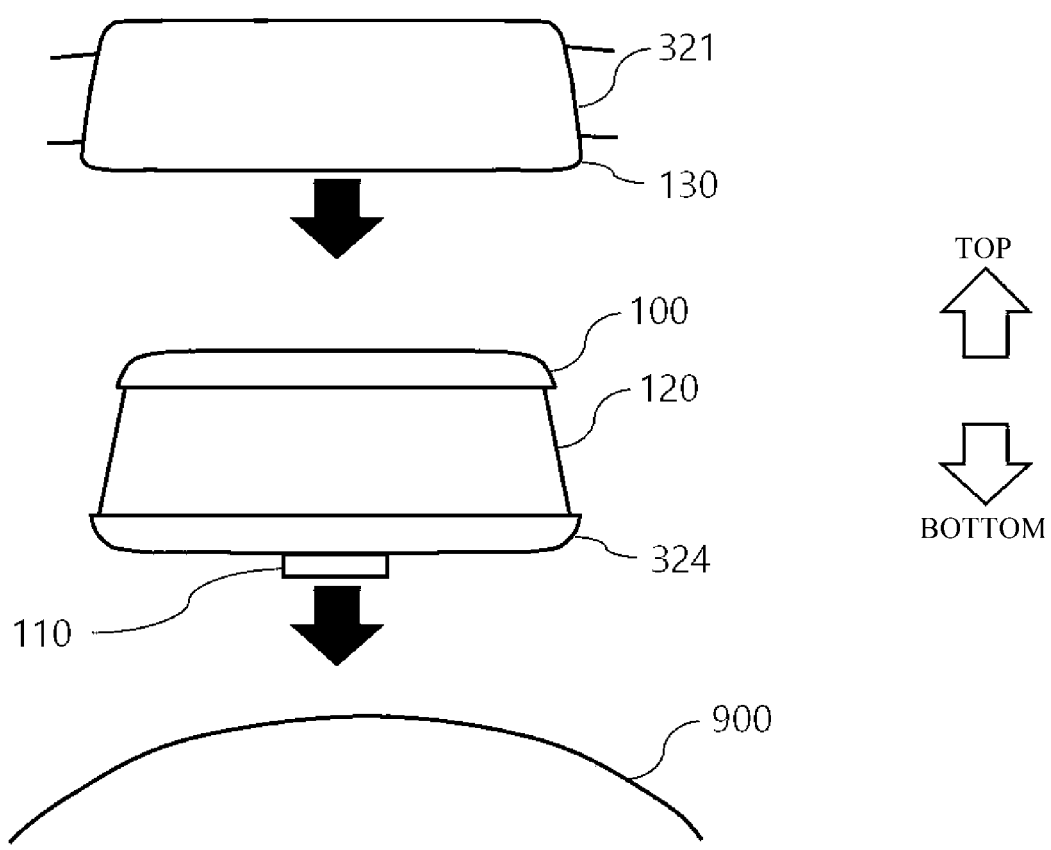
FIG. 4 is a view illustrating a main body support portion and a main body engagement method, according to an exemplary embodiment of the present invention.
Figure 5A:
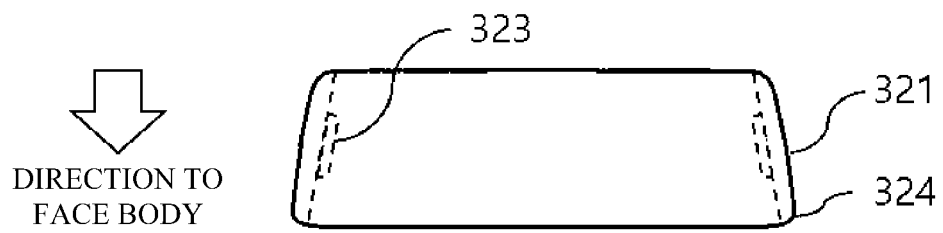
FIGS. 5A and 5B are views illustrating the main body support portion and the main body engagement method, according to an exemplary embodiment of the present invention.
Figure 5B:
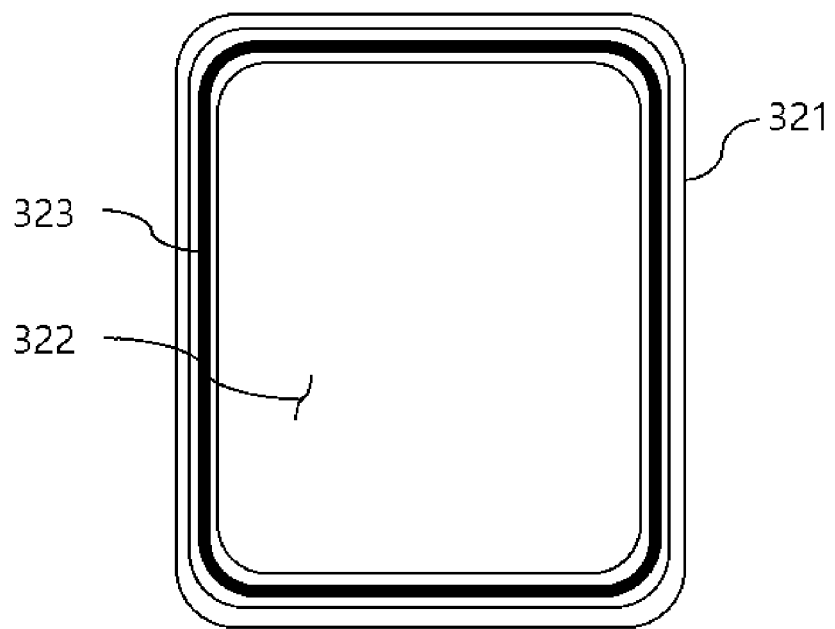

FIGS. 4 to 5B are views illustrating the main body support portion and a main body engagement method, according to an exemplary embodiment of the present invention.

As illustrated in FIG. 5B, the main body support portion 321 may be separable from the main body 100, and a hole 322 is formed in the main body support portion 321 in a direction away from the surface of the body 900, so that the main body 100 may be engaged with the main body support portion 321.

Further, the hole 322 has one opening facing the body 900 and having an area larger than that of the other opening as illustrated in FIG. 5A, and it is preferable that a groove 120 to which the main body support portion 321 is fixed is formed along the side surface of the main body 100 as illustrated in FIG. 4.

It is preferable that a protrusion engaged with the groove 120 is formed along an inner surface of the main body support portion 321 accordingly.

As illustrated in FIGS. 5A and 5B, according to an exemplary embodiment of the present invention, the body-attachable biometric signal acquisition device 10 may further include a ring 323 fused to an inner surface of the hole 322 along the inner surface of the hole 322, and formed of a material having a hardness higher than that of a material of the main body support portion 321.

The ring 323 may provide support to the main body support portion 321 formed of the an elastic material, such that the main body support portion 321 may firmly support the main body 100. The ring 323 is preferably formed of a synthetic resin material having a high hardness, such as a melamine resin or an acrylonitrile butadiene styrene (ABS) resin, or metal.

It is preferable that the sensor 110 is formed on a lower surface of the main body 100, and roundings 130 and 324 are formed at corners of the main body and the main body support portion as illustrated in FIG. 4.

According to an exemplary embodiment of the present invention, the main body support portion 321 may include a top cover supporting an upper portion of the main body to prevent the main body 100 from being separated.

The main body support portion 321 may be separable from the main body 100. The first hole 322 may be formed in the main body support portion 321 in a direction away from the surface of the body 900, so that the main body 100 may be engaged with the main body support portion 321. Further, a rugged portion that may support the pressure 850 generated between the sensor 110 and the surface of the body 900 may be formed on a surface of the first hole 322 with which the main body 100 is engaged.

The rugged portion may have a curved cross section.

The rugged portion may have an S-letter shaped cross section.

The main body support portion 321 may include a support supporting a lower portion of the main body 100 to prevent the main body 100 from slipping on the surface of the body 900.

The main body support portion 321 may have any one of a rectangular shape, a square shape, a circular shape, or an oval shape, when viewed from above.

It is preferable that the roundings 130 are formed at corners of the main body support portion 321 that face the body 900, among the corners of the main body support portion 321 as illustrated in FIG. 4.

The outer cover 330 may be formed of a fabric material and enclose the elastic restoring moment generating portion 325.

It is preferable that the elastic restoring moment generating portion 325 includes one or more sewing holes 326 and is sewed to the outer cover 330 through the sewing holes 326 by using sewing thread 327 as illustrated in FIG. 1.

Figure 10A:
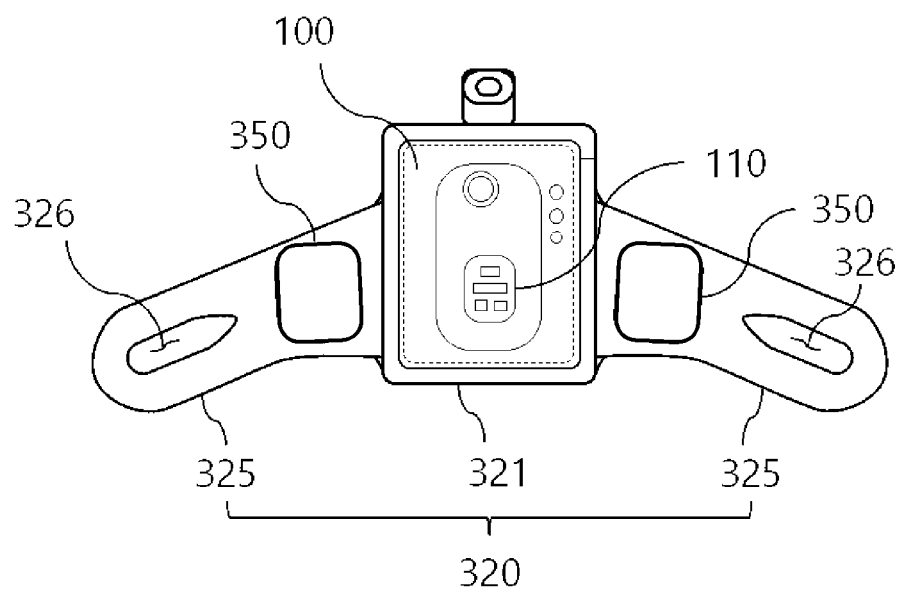
FIGS. 10A and 10B are views illustrating a body-attachable biometric signal acquisition device according to an exemplary embodiment of the present invention.
Figure 10B:
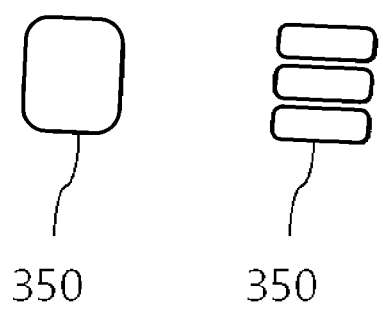

FIGS. 10A and 10B are views illustrating a body-attachable biometric signal acquisition device according to an exemplary embodiment of the present invention. As illustrated in FIG. 10, the first strap 310 includes two straps each extending in a U-letter shape from each of the opposite outer side surfaces of the main body support portion 321, the first fixing portion 300 includes air cushions 350 each having an opened or closed cavity therein, and the air cushions 350 each are formed on a surface of each of the two straps at a position close to the main body 100 when the first strap 310 winds the body 900 to fasten the main body 100 and the first fixing portion 300 to the body 900, the surface of each of the two straps being a surface facing the body 900. The air cushion 350 supports the surface of the body 900 to prevent the main body 100 from wobbling in a case where an external force is applied to the gap formed between the straps and the body due to the elastic restoring moment generated when the first strap 310 winds the body 900 to fasten the main body 100 and the first fixing portion 300 to the body 900, and an additional gap formed due to body size variation caused by fast growth of an infant. Each of the two straps may include the framework 320 formed of the elastic material, and the outer cover 330 enclosing the framework 320 or part of the framework 320, or fused to the framework 320, and formed of a fabric material or an elastic material.

The air cushion 350 solves a problem that a gap is formed between the strap and the body 900 when the elastic restoring moment 800 is generated, and a size and a shape of the body 900 greatly vary between individuals and at difference ages because infants grow fast to thereby enable stable acquisition of a biometric signal.

Further, it is preferable that the air cushion 350 is formed integrally with or attached to the framework 320 as illustrated in FIG. 10A, and a volume of the cavity in the air cushion 350 is decreased as the pressure 850 is increased.

As illustrated on the right side of FIG. 10B, a plurality of air cushions 350 may be provided in parallel.

Figure 11A:
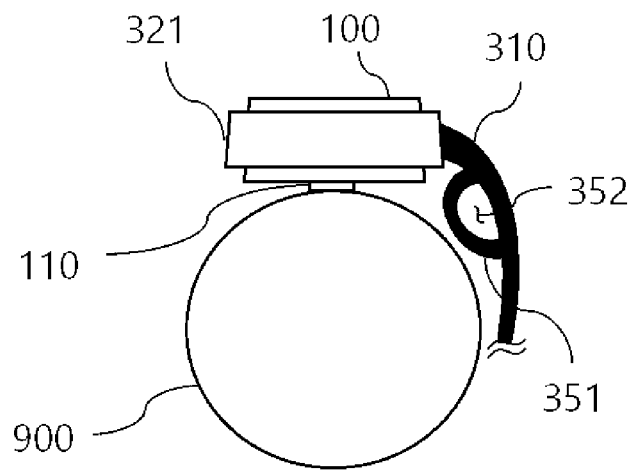
FIGS. 11A and 11B are views illustrating a body-attachable biometric signal acquisition device according to an exemplary embodiment of the present invention.
Figure 11B:
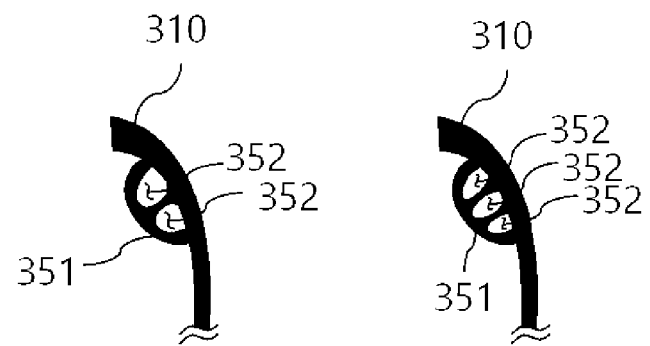

FIGS. 11A and 11B are views illustrating a body-attachable biometric signal acquisition device according to an exemplary embodiment of the present invention. As illustrated in FIGS. 11A and 11B, the air cushion 350 may include at least one arc-shaped member 351 including at least one second hole 352 formed in a direction perpendicular to a direction in which the outer covers 330 each extend in the U-letter shape from the each of opposite outer side surfaces of the main body support portion 321.

Further, as illustrated in FIG. 11B, the number of second holes 352 formed in the arc-shaped member 351 may be plural.

The air cushion 350 may be formed of a fabric material and formed on the surface of each outer cover 330 at a position close to the main body 100, the surface of each outer cover 330 being a surface facing the body 900 when the first strap 310 winds the body 900 to fasten the main body 100 and the first fixing portion 300 to the body 900.

The air cushion 350 may include at least one arc-shaped member 351 including at least one second hole 352 formed in the direction perpendicular to the direction in which the outer covers 330 each extend in the U-letter shape from the each of opposite outer side surfaces of the main body support portion 321.

It is preferable that the outer cover 330 is fused to the elastic restoring moment generating portion 325 and formed of an elastic material having a hardness lower than that of the elastic restoring moment generating portion 325, and the air cushion 350 is formed on the surface of each outer cover 330 at a position close to the main body 100, the surface of each outer cover 330 being a surface facing the body 900 when the first strap 310 winds the body 900 to fasten the main body 100 and the first fixing portion 300 to the body 900.

The air cushion 350 may include at least one arc-shaped member 351 including at least one second hole 352 formed in the direction perpendicular to the direction in which the outer covers 330 extend from the opposite outer side surfaces of the main body support portion 321, respectively.

The number of second holes 352 formed in the arc-shaped member 351 may be plural.

It is preferable that the outer cover 330 is formed of a fabric material, is connected to the elastic restoring moment generating portion 325 and the air cushion 350 with Velcro, and encloses the elastic restoring moment generating portion 325 and the air cushion 350.

Opposite sides of the elastic restoring moment generating portion 325 each have a ring shape with an empty middle portion, and the outer cover 330 may be sewed along an inner boundary of the ring shape.

It is preferable that linings 331a and 331b positioned at one surface of the outer cover 330, and outer shells 332a and 332b positioned at another surface opposite to the one surface are formed of one or more layers of fabric material, the one surface facing the surface of the body 900 when the first fixing portion 300 winds the body 900 to fasten the main body 100 to the body 900, and the elastic restoring moment generating portion 325 adheres or is fused between the linings 331a and 331b, and the outer shells 332a and 332b, as illustrated in FIG. 3.

It is preferable that the linings 331a and 331b are formed of a material softer than that of the outer shells 332a and 332b, the outer shells 332a and 332b are formed of a material that is more easily attachable with Velcro than that of the linings 331a and 331b is, and the linings 331a and 331b, and the outer shells 332a and 332b adhere or are fused to the elastic restoring moment generating portion 325 by using an adhesive, an adhesion film, or a synthetic resin material.

The elastic restoring moment generating portion 325 may include one or more sewing holes 326 for sewing and may be sewed to the outer cover 330 through the sewing holes 326.

It is preferable that the outer cover 330 is fused to a surface or part of the surface of the elastic restoring moment generating portion 325, the surface being a surface facing the body 900 when the first fixing portion 300 winds the body 900 to fasten the main body 100 to the body 900, the outer cover 330 is formed of an elastic material having a hardness lower than that of the elastic restoring moment generating portion 325, and the outer cover 330 and the elastic restoring moment generating portion 325 are fused to each other while forming an inclined surface at a predetermined angle.

When viewed from a side of the first fixing portion 300, the outer cover 330 and the elastic restoring moment generating portion 325 may be fused in a diagonal line shape, a V-letter shape, or a saw-tooth shape.

It is preferable that the outer cover 330 is fused to a surface or part of the surface of the elastic restoring moment generating portion 325, the surface being opposite to the surface facing the body 900.

Figure 12A:
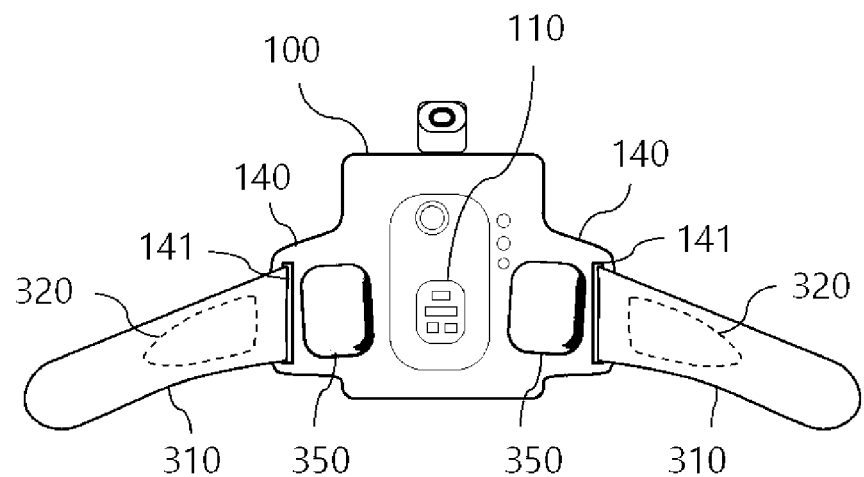
FIGS. 12A and 12B are views illustrating a body-attachable biometric signal acquisition device according to an exemplary embodiment of the present invention.
Figure 12B:
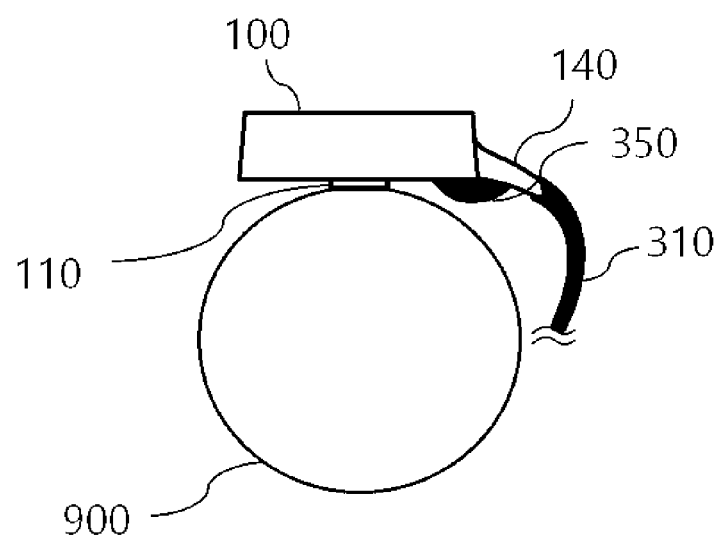

FIGS. 12A and 12B are views illustrating a body-attachable biometric signal acquisition device according to an exemplary embodiment of the present invention. As illustrated in FIG. 12A, the frameworks 320 may be formed to be spaced apart from opposite outer side surfaces of the main body 100 by a predetermined distance, respectively, and may each extend in a U-letter shape from each of the opposite outer side surfaces of the main body 100.

The frameworks 320 each have a distal end separated from the surface of the body 900 when the sensor 110 is brought into contact with an attaching portion of the body 900. It is preferable that the frameworks 320 each have one end connected to the main body support portion 321, the one end having a cross section 328b which is taken in a direction perpendicular to a length direction of the framework 320 and of which a thickness and an area are larger than those of a cross section 328a of the distal end.

A protruding portion 140 may be formed at each of the opposite outer side surfaces of the main body 100, and a slot 141 to which the first strap 310 may be detachably attached may be formed at a distal end of the protruding portion 140.

It is preferable that the biometric signal acquisition device 10 further includes outer covers 330 fused to a surface or part of the surface of the framework 320, the surface being opposite to the surface facing the body 900.

The frameworks 320 each have a distal end separated from the surface of the body 900 when the sensor 110 is brought into contact with an attaching portion of the body 900, and the frameworks 320 may each include a first elastic material member, and a second elastic material member fused to a distal end of the first elastic material member in a length direction and having a hardness lower than that of the first elastic material member by a predetermined value.

The biometric signal acquisition device 10 may further include air cushions 350 each having a cavity therein or padded, and formed on end portions of the opposite outer side surfaces of the main body 100, the end portions facing the body 900, the air cushion 350 supports the surface of the body 900 to prevent the main body 100 from wobbling in a case where an external force is applied to a gap formed between the straps and the body due to the elastic restoring moment generated when the first strap 310 winds the body 900 to fasten the main body 100 and the first fixing portion 300 to the body 900, and an additional gap formed due to body size variation caused by fast growth of an infant, and the air cushion 350 may further include at least one arc-shaped member 351 including at least one second hole 352 formed in a direction perpendicular to a direction in which the outer covers 330 each extend in the U-letter shape from the each of the opposite outer side surfaces of the main body support portion 321.

It is preferable that the biometric signal acquisition device 10 further includes the outer covers 330 formed of an elastic material having a hardness lower than that of the material of the framework 320, the outer cover 330 is fused to a surface or part of the surface of the framework 320, the surface being a surface facing the body 900 when the first fixing portion 300 winds the body 900 to fasten the main body 100 to the body 900, and the outer cover 330 encloses the framework 320 or the outer cover 330 and the framework 320 are fused to each other while forming an inclined surface at a predetermined angle.

When viewed from a side of the first fixing portion 300, the outer cover 330 and the framework 320 may be fused in a diagonal line shape, a V-letter shape, or a saw-tooth shape.

It is preferable that the outer cover 330 is fused to a surface or part of the surface of the framework 320, the surface being opposite to the surface facing the body 900.

It is preferable that in a case where the first fixing portion 300 winds the body 900 to fasten the main body 100 to the body 900, a gap 700 is present between an outer surface of the outer cover 330 under the elastic restoring moment generating portion 325 and the surface of the body 900 (see FIG. 2).

Further, the outer cover 330 may be fused to the elastic restoring moment generating portion 325 and may be formed as a strap formed of an elastic material having a hardness lower than that of the material of the elastic restoring moment generating portion 325.

It is preferable that a cross section of the first fixing portion 300 taken in a direction perpendicular to the length direction at a position corresponding to each of one ends of the elastic restoring moment generating portions 325 has a thickness and an area larger than those of a cross section of the first fixing portion 300 at a position corresponding to each of distal ends of the elastic restoring moment generating portion 325.

As described above, as the area of the cross section of the first fixing portion 300 varies in the length direction, the gap 700 may be formed between the first fixing portion 300 and the surface of the body 900 at a position close to the main body support portion 321, and the first fixing portion 300 may closely adhere to the surface of the body 900 at a position distant from the main body support portion 321.

Further, it is preferable that the first fixing portion 300 has a higher hardness at the position corresponding to each of the one ends of the elastic restoring moment generating portions 325 than at the position corresponding to each of the distal ends of the elastic restoring moment generating portion 325.

It is preferable that the outer cover 330 is fused to a surface or part of the surface of the elastic restoring moment generating portion 325, the surface of the elastic restoring moment generating portion 325 being a surface facing the body 900, and the outer cover 330 and the elastic restoring moment generating portion 325 is fused to each other while being inclined.

An entire length of the framework 320 is less than a circumference of a portion of the body 900 on which the first fixing portion 300 winds. The first fixing portion 300 includes fasteners 341 and 342 formed at opposite distal ends of the first fixing portion 300, respectively, and fastened to each other, and it is preferable that a fastening position or a fastening area of the fasteners 341 and 342 may be adjusted according to size variation of the body 900.

The outer cover 330 may have a hardness lower than that of the elastic restoring moment generating portion 325 by a predetermined value.

According to an exemplary embodiment of the present invention, the predetermined value is preferably 1 or more.

Figure 6:
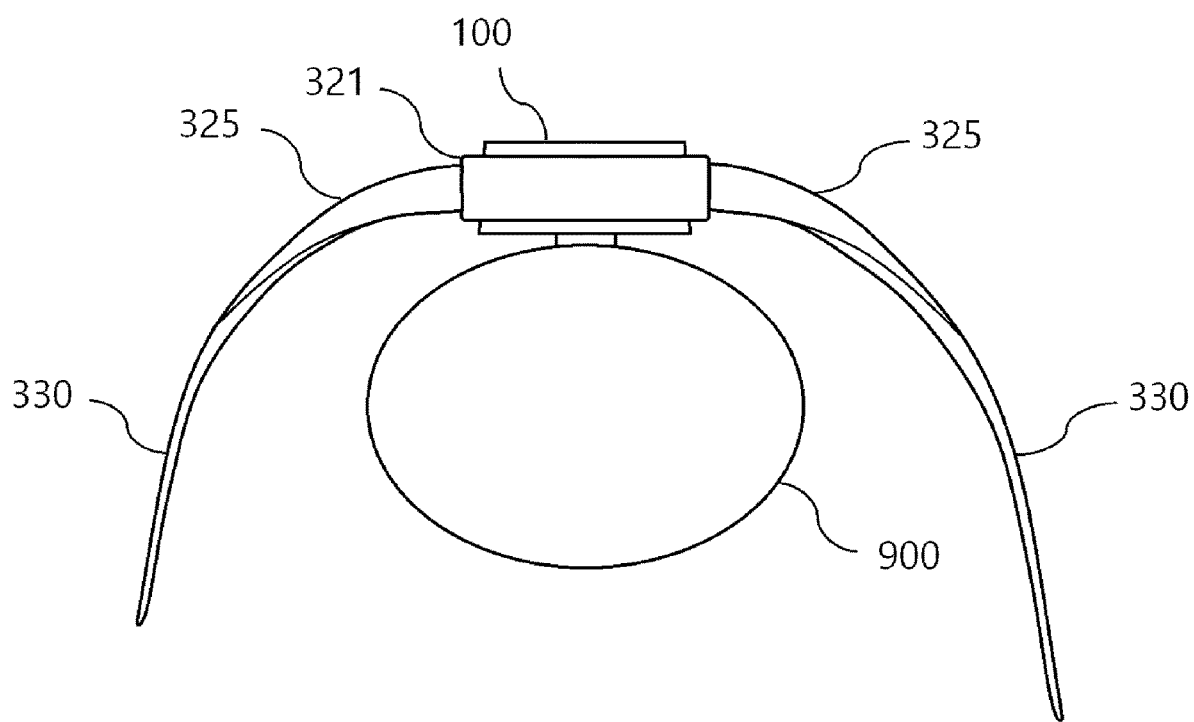
FIG. 6 is a view illustrating a body-attachable biometric signal acquisition device according to an exemplary embodiment of the present invention.

FIG. 6 is a view illustrating a body-attachable biometric signal acquisition device according to an exemplary embodiment of the present invention.

It is preferable that the outer cover 330 is fused while entirely or partially enclosing the elastic restoring moment generating portion 325 as illustrated in FIG. 3, or is fused to a surface or a part of the surface of the elastic restoring moment generating portion 325 as illustrated in FIG. 6.

Figure 7A:
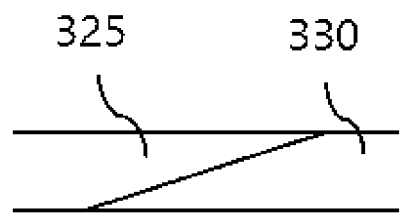
FIGS. 7A to 7C are views each illustrating part of a first fixing portion according to an exemplary embodiment of the present invention.
Figure 7B:
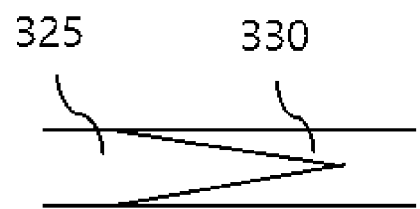
Figure 7C:
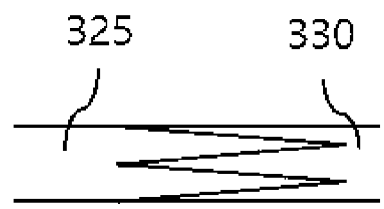

FIGS. 7A to 7C are views each illustrating part of the first fixing portion according to an exemplary embodiment of the present invention. It is preferable that when the outer cover 330 is fused to a surface or a part of the surface of the elastic restoring moment generating portion 325, the outer cover 330 and the elastic restoring moment generating portion 325 are fused in a diagonal line shape (FIG. 7A), a V-letter shape (FIG. 7B), or a saw-tooth shape (FIG. 7C) when viewed from a side of the first fixing portion 300 as illustrated in FIGS. 7A to 7C.

Further, the biometric signal acquisition device 10 may further include a second fixing portion 400 disposed parallel to the first fixing portion 300 and winding the body 900.

FIG. 8 is a view illustrating a body-attachable biometric signal acquisition device according to an exemplary embodiment of the present invention. In FIG. 1, the bottom portion of the outer cover 330 coming into contact with the surface of the body 900 is omitted.

As illustrated in FIG. 8, the sewing hole 326 is formed to be long in each of opposite elastic restoring moment generating portions 325, the opposite elastic restoring moment generating portions 325 each have a ring shape with an empty middle portion, and portions of the elastic restoring moment generating portions 325, that, respectively, correspond to positions at which the elastic restoring moment generating portions 325 are connected to the main body support portion 321, and distal ends of the elastic restoring moment generating portions 325 may be sewed to the outer covers 330 enclosing the elastic restoring moment generating portions 325.

Back stitching may be added to a portion of the outer cover 330 along an inner circumference of the ring shape with an empty middle portion to enable easy back stitching while preventing the portion of the outer cover 330 from floating off. In this case, a weight of the framework 320 may also be reduced.

It is preferable that the elastic restoring moment generating portions 325 each have one end connected to the main body support portion 321, the one end having a cross section 328b which is taken in a direction perpendicular to a length direction of the elastic restoring moment generating portion 325 and of which a thickness and an area are larger than those of a cross section 328a of the distal end.

As illustrated FIG. 8, the one end of the elastic restoring moment generating portion 325 connected to the main body support portion 321 has the cross section 328b of which the thickness and the area are larger than those of the cross section 328a of the distal end. As the area of the cross section of the elastic restoring moment generating portion 325 varies in the length direction, the gap 700 may be formed between the outer cover 330 and the surface of the body 900 at a position close to the main body support portion 321, and the outer cover 330 may closely adhere to the surface of the body 900 at a position distant from the main body support portion 321.

Meanwhile, the elastic restoring moment generating portion 325 may include a first elastic material strap connected to the main body support portion 321, and a second elastic material strap fused or adhering to the first elastic material strap, and having a hardness higher than that of the first elastic material strap by a predetermined value.

According to an exemplary embodiment of the present invention, the predetermined value is preferably 1 or more.

Figure 9:
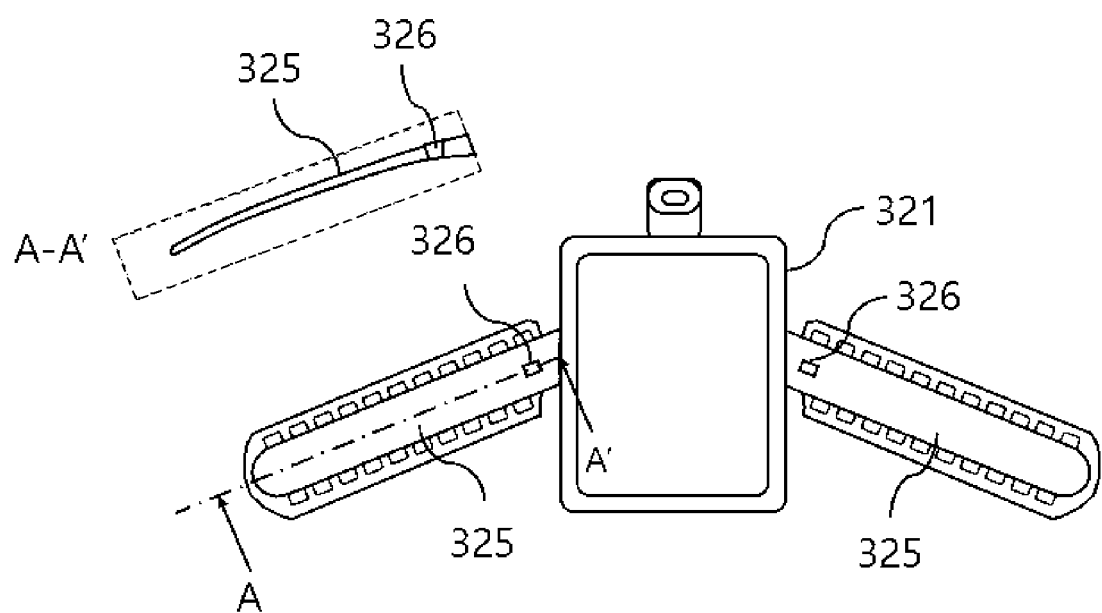
FIG. 9 is a view illustrating a framework according to an exemplary embodiment of the present invention.

FIG. 9 is a view illustrating a framework according to an exemplary embodiment of the present invention. As illustrated in FIGS. 9 and 1, holes for sewing may be formed along a circumference of the elastic restoring moment generating portion 325. In particular, the holes for sewing may be connected to an edge of each of the elastic restoring moment generating portions 325 (see FIG. 9), or may be formed in a protrusion shape and connected at predetermined intervals (see FIG. 1) to sew the outer cover 330, thereby connecting the framework 320 and the outer cover 330 to each other.

FIG. 13 is a view illustrating a state in which a body-attachable biometric signal acquisition device is attached to a body, according to an exemplary embodiment of the present invention. As illustrated in FIG. 13, the biometric signal acquisition device 10 that is attachable to the body 900 according to an exemplary embodiment of the present invention may include: a main body 100 including a sensor 110 acquiring a biometric signal in a state of closely adhering to a surface of the body 900; a first fixing portion 300 which winds the body 900 to fix the main body 100 and to which the main body 100 is detachably attached; and a second fixing portion 400 disposed parallel to the first fixing portion 300 and winding the body 900.

The first fixing portion 300 may include a first strap 310 extending in a transverse direction of the main body 100, and the second fixing portion 400 may include a second strap 410 disposed parallel to the first strap 310 and extending bidirectionally.

The second strap 410 may prevent the biometric signal acquisition device 10 from slipping down on the body 900.

FIG. 14 is a view illustrating a body-attachable biometric signal acquisition device according to an exemplary embodiment of the present invention. As illustrated in FIG. 14, a distance between the first strap 310 and the second strap 410 becomes broad toward distal ends of the first strap 310 and the second strap 410.

Further, the first strap 310 and the second strap 410 may each have a V-letter shape or a U-letter shape facing the same direction (see FIG. 14).

Such a V-letter shape or a U-letter shape facing the same direction may increase a degree of close adherence to the body and prevent slipping down.

It is preferable that the body 900 is any one of an upper arm, a lower arm, or a lower leg of a human. An upper arm, a lower arm, and a lower leg of a human has a streamlined shape with a convex middle portion, and thus the second strap 410 may effectively prevent the biometric signal acquisition device 10 from slipping down toward an ankle.

As illustrated in FIG. 13, in a case where the body 900 is a lower leg of a human, and the biometric signal acquisition device 10 is attached to the lower leg, it is preferable that the main body 100 is positioned at an inner side of a portion below a calf of the lower leg to closely adhere to the lower leg.

A toe has been used by an existing medical instrument used in a hospital to obtain a biometric signal such as a PPG signal from an infant or a patient. Recently, there have been several attempts to use a sole, a thigh, a wrist, or the like. However, in order to stably acquire a biometric signal also in a general domestic environment, the biometric signal acquisition device needs to be attached to a portion to enable easy attachment, detachment, and support, and significantly reduce inconvenience of an infant or a patient, and a lower leg may be appropriate.

Further, the biometric signal acquisition device 10 may further include a first connection portion 500 including one or more straps fixing the first strap 310 and the second strap 410 to each other.

FIGS. 15A to 19C are views each illustrating a state in which a body-attachable biometric signal acquisition device is attached to a body, according to an exemplary embodiment of the present invention. FIGS. 15A, 16A, 17A, 18A, and 19A each are a view when viewed from an inner side of the right lower leg of a human, FIGS. 15B, 16B, 17B, 18B, and 19B each are a view when viewed from behind the right lower leg, and FIGS. 15C, 16C, 17C, 18C, and 19C each are a view when viewed from an outer side of the right lower leg.

Figure 15A:
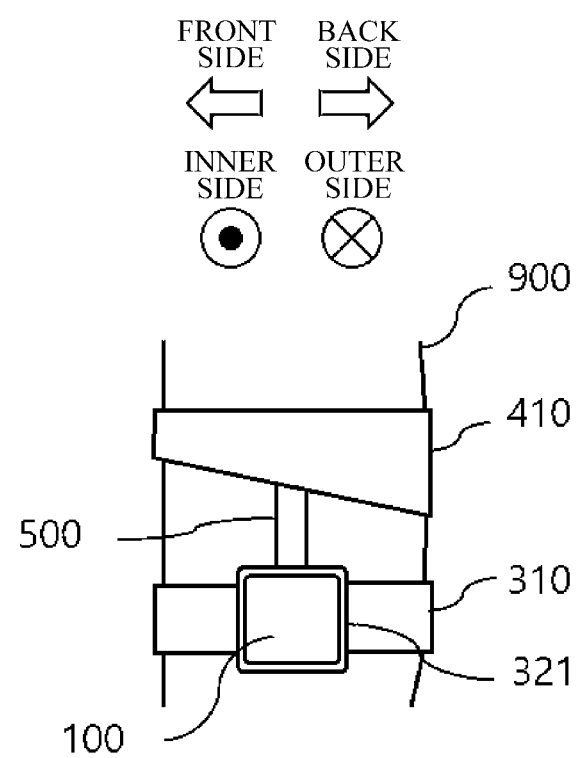
FIGS. 15A to 15C are views each illustrating a state in which a body-attachable biometric signal acquisition device is attached to a body, according to an exemplary embodiment of the present invention.
Figure 15B:
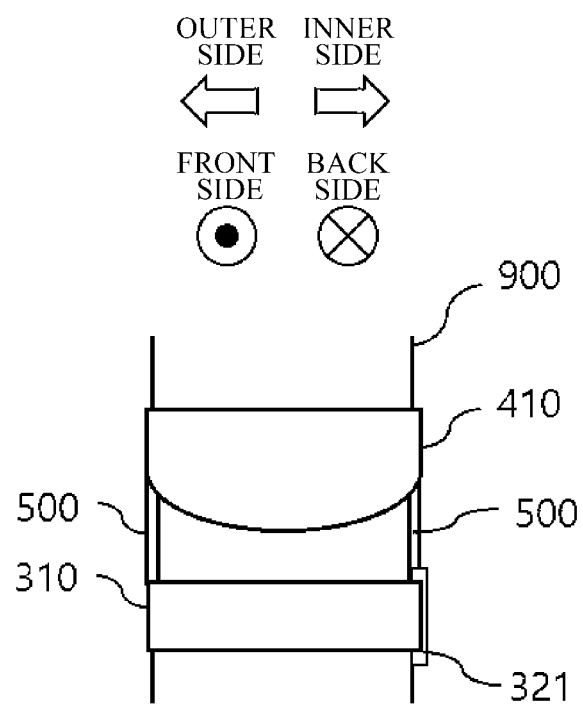
Figure 15C:
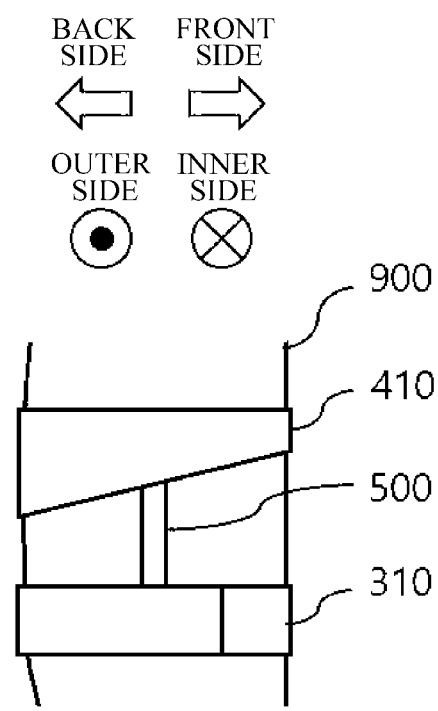

As illustrated in FIGS. 15A to 15C, according to an exemplary embodiment of the present invention, the second strap 410 may have a streamlined shape in which a portion of the second strap 410 that corresponds to a back portion of a calf of the lower leg has a lower line curved toward the first strap 310, to thereby support the calf when the biometric signal acquisition device 10 is attached to the lower leg.

Figure 16A:
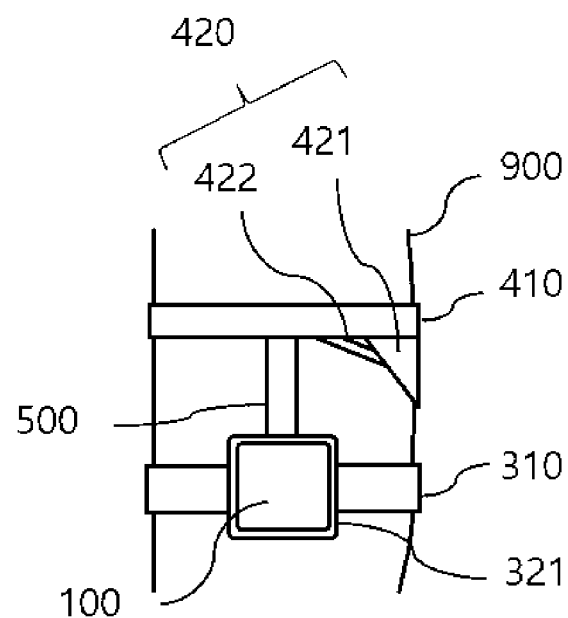
Figure 16B:
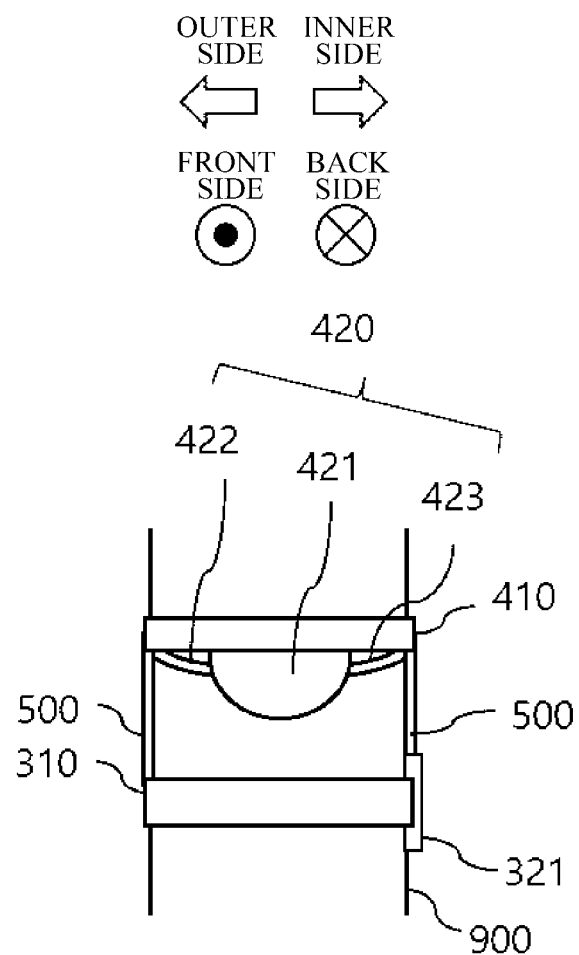

As illustrated in FIGS. 16A to 16C, according to an exemplary embodiment of the present invention, the second fixing portion 400 may further include an auxiliary strap 420 fixed to the second strap 410 in a direction toward the first strap 310 and supporting the calf when the biometric signal acquisition device 10 is attached to the lower leg.

Such an auxiliary strap 420 may prevent the biometric signal acquisition device 10 from rotating in a circumferential direction of the body 900. Further, the second strap 410 may enable a secure wearing even in a case where a size or a shape of the body 900 varies, or the body 900 moves.

Further, the auxiliary strap 420 may include a strap 421 having a streamlined shape in which a portion of the strap 431 that corresponds to a back portion of the calf of the lower leg has a lower line curved toward the first fixing portion 300.

Further, the auxiliary strap 420 may further include two straps 422 and 423 supporting opposite side of the lower line of the streamlined shape and connected to the second strap 410.

Figure 17B:
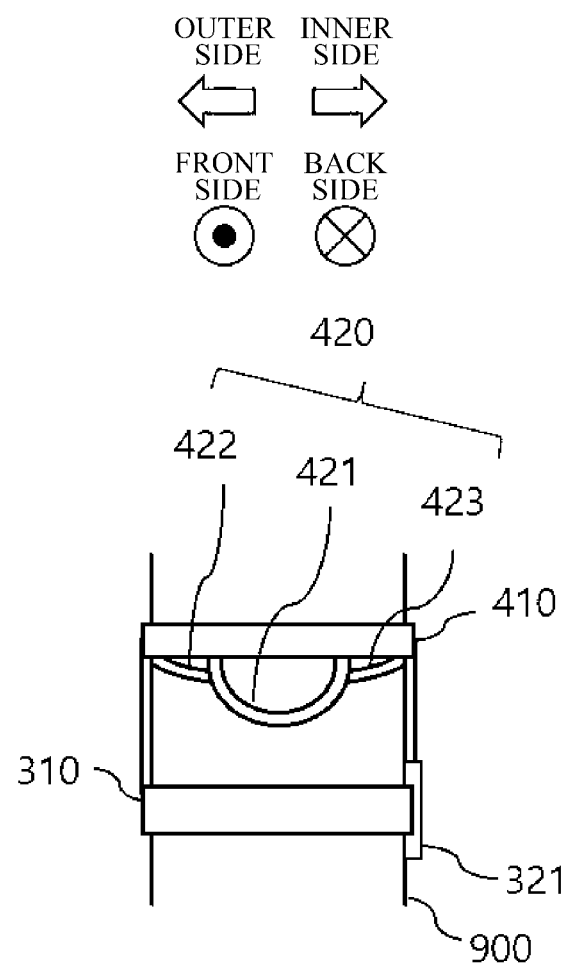

According to an exemplary embodiment of the present invention, it is preferable that the strap 421 has a streamlined shape with an empty middle portion as illustrated in FIGS. 17A to 17C.

Figure 18A:
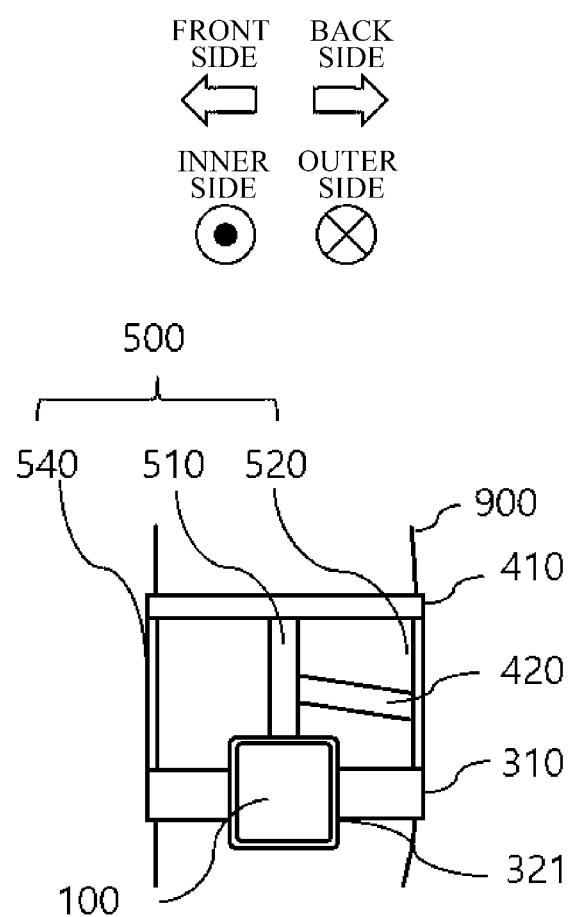
Figure 18B:
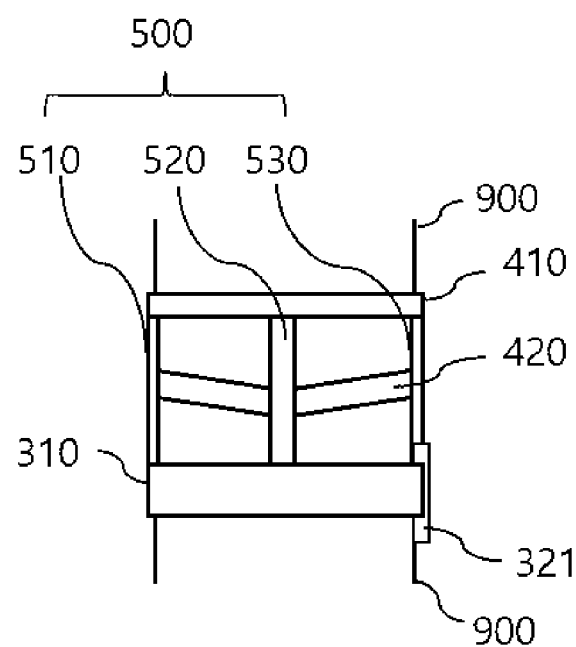

As illustrated in FIGS. 18A to 18C, according to an exemplary embodiment of the present invention, the first connection portion 500 may include a first connection strap 510 positioned on an inner surface of the calf when the biometric signal acquisition device 10 is attached to the lower leg, a second connection strap 520 positioned on a back surface of the calf, a third connection strap 530 positioned on an outer surface of the calf, and a fourth connection strap 540 positioned on a front surface of the calf, and the auxiliary strap 420 may connect a middle portion of the first connection strap 510 and a middle portion of the second connection strap 520 to each other, and connect the middle portion of the second connection strap 520 and a middle portion of the third connection strap 530 to each other.

Figure 19A:
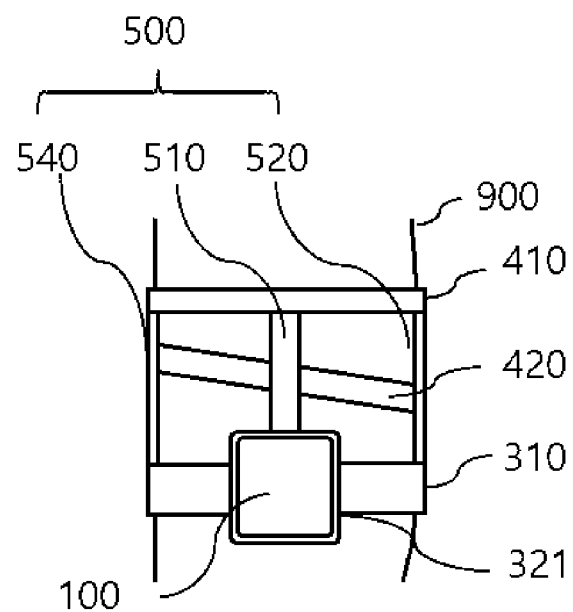
Figure 19B:
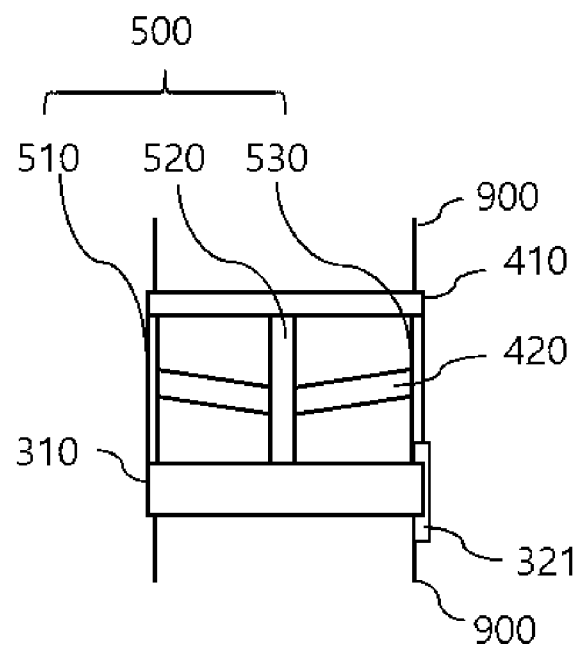
Figure 20A:
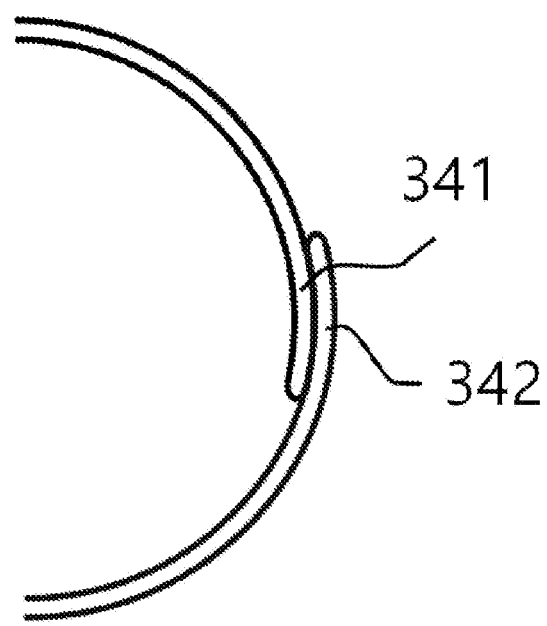
FIGS. 20A and 20B are views illustrating a fastened state of a fastening portion according to an exemplary embodiment of the present invention.
Figure 20B:
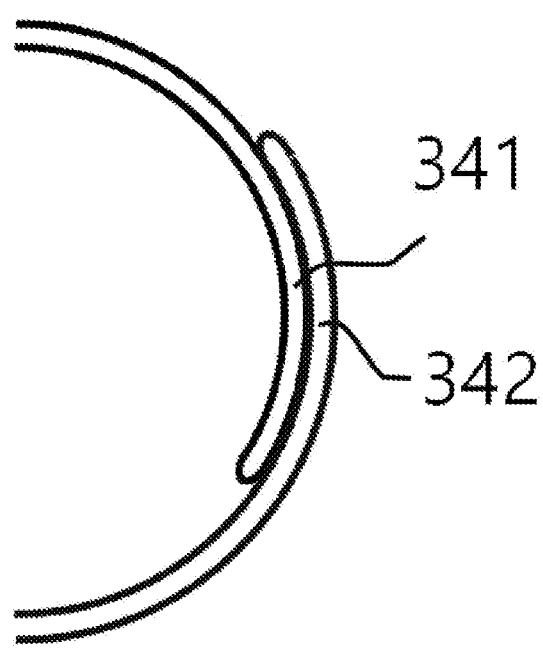
Figure 21A:
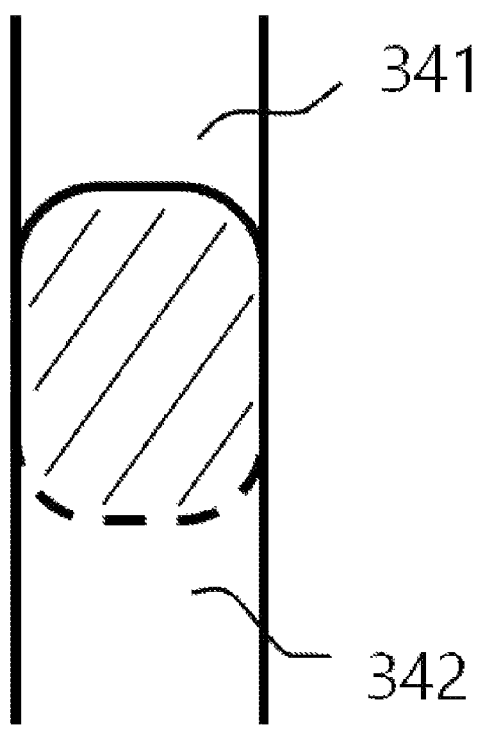
FIGS. 21A and 21B are views illustrating a fastened state of a fastening portion according to an exemplary embodiment of the present invention.
Figure 21B:
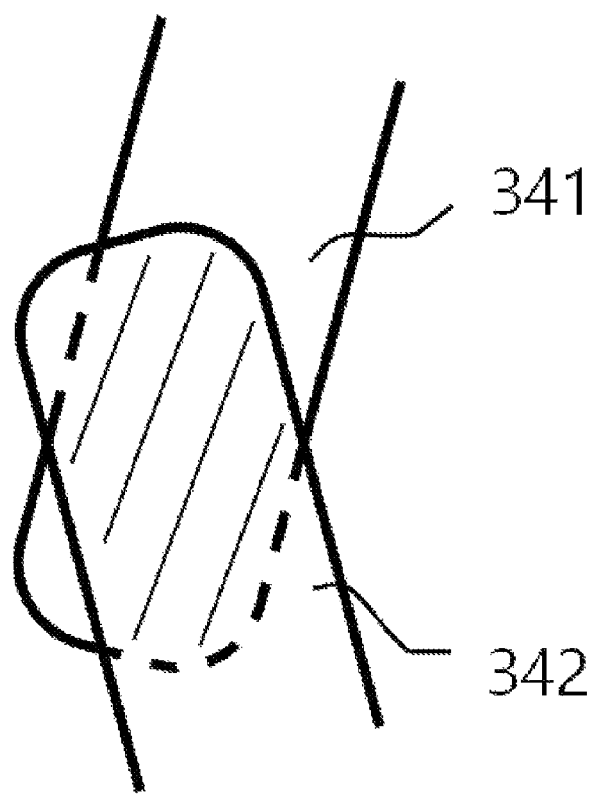

As illustrated in FIGS. 19A to 19C, according to an exemplary embodiment of the present invention, the auxiliary strap 420 may connect the middle portion of the third connection strap 530 and a middle portion of the fourth connection strap 540 to each other, and connect the middle portion of the fourth connection strap 540 and the middle portion of the second connection strap 520 to each other.

FIGS. 20A to 21B are views illustrating a fastened state of a fastening portion according to an exemplary embodiment of the present invention. As illustrated in FIGS. 20A to 21B, each of the first strap 310, the second strap 410, and the auxiliary strap 420 includes fasteners 341 and 342 formed at opposite distal ends and fastened to each other, and it is preferable that one or more of a fastening position (see FIGS. 20A and 20B) and a fastening angle (see FIGS. 21A and 21B) of the fasteners 341 and 342 may be adjusted by a user so that the first strap 310, the second strap 410, and the auxiliary strap 420 may closely adhere to the body 900.

Since a curvature of a body varies between individuals, the straps may closely adhere to a curved surface of a calf with a uniform pressure by using a structure in which opposite sides of each strap may be fixed at a certain angle.

Such a structure in which opposite sides of each strap may be fixed at a certain angle may be implemented in a manner in which, for example, Velcro, a buckle, or a plurality of buttons, snap fasteners, or magnets are provided on the fasteners 341 and 342. In particular, in a case where the snap fasteners or magnets are provided, it is preferable that a non slip material adheres to, is fused to, or is coated on contact surfaces of the straps, such that the opposite fasteners do not become loose and are fixed to each other without rotating with respect to each other.

Further, a length of the first strap 310 may be adjusted when the first strap 310 is attached to the body 900 by adjusting a fastening position.

Such an adjustment of the fastening position to adjust the length of the first strap 310 may be implemented in a manner in which, for example, Velcro, a buckle, or a plurality of buttons, snap fasteners, or magnets are provided on the fasteners 341 and 342.

Further, it is preferable that a distance between a lower end of the auxiliary strap 420 that faces the first strap 310, and the second strap 410 becomes narrow toward a front side of the calf and becomes broad toward a back side of the calf.

The biometric signal acquisition device 10 may further include a second connection portion (not illustrated) including one or more straps to maintain a distance between the auxiliary strap 420 and the second strap 410, and it is preferable that lengths of the one or more straps included in the first connection portion 500 are adjustable, and in a case where the number of one or more straps included in the first connection portion 500 is two or more, lengths of the one or more straps may be adjusted individually. Further, it is preferable that lengths of the one or more straps included in the second connection portion (not illustrated) are adjustable, and in a case where the number of one or more straps included in the second connection portion (not illustrated) is two or more, lengths of the one or more straps may be adjusted individually.

Further, each of the first connection portion 500 and the second connection portion (not illustrated) may include one or more of fasteners (not illustrated) including snap fasteners, a plurality of buttons, connection rings, Velcro, magnets, and hook and eye clasps.

In addition, it is preferable that a non-loose and non-slip material adheres to, is fused to, or is coated on portions of the first connection portion 500 and the second connection portion (not illustrated) that are adjacent to the one or more of the fasteners (not illustrated), or are spaced apart from the fasteners (not illustrated) by a predetermined distance.

The second strap 410 and the auxiliary strap 420 is preferably formed of an elastic material.

Further, a protrusion (not illustrated) or a groove (not illustrated) may be formed on or in a surface of at least one of the first strap 310, the second strap 410, or the auxiliary strap 420, the surface facing the surface of the body 900. Such a protrusion or groove may enable ventilation to prevent skin from sweating.

It is preferable that lengths of the one or more straps included in the first connection portion 500 are adjustable, and in a case where the number of one or more straps included in the first connection portion 500 is two or more, lengths of the one or more straps may be adjusted individually.

Further, it is preferable that the second fixing portion 400 may be detachably attached to the first fixing portion 300.

FIG. 22 is a view illustrating forms in which the first fixing portion and the first connection portion of a body-attachable biometric signal acquisition device are fastened to each other, according to an exemplary embodiment of the present invention. As illustrated in FIG. 22, the first fixing portion 300 and the first connection portion 500 may be detachably fastened to each other by using various members such as Velcro (FIG. 22A), a protrusion and a fitting hole (FIG. 22B), and a trigger lobster clasp (FIG. 22C).

According to various exemplary embodiments of the present invention described above, the body-attachable biometric signal acquisition device according to the present invention may maintain close adherence of the sensor to the skin by using an elastic restoring moment to stably acquire a biometric signal.

Further, the body-attachable biometric signal acquisition device according to the present invention may restore adherence to the body with a restoring force when movement or application of an external force stops even in a case where light leakage or slipping occurs due to the movement or the temporary application of the external force.

Further, it is possible to solve the problem that the wobbling of the main body due to an external impact occurs, the wobbling being caused by a gap formed between the strap and the body due to body size variation when the elastic restoring moment is generated, by using a buffering function of the air cushion formed on a surface of the first fixing portion that is brought into contact with the body and is close to the main body, thereby making it possible to acquire a stable biometric signal.

Further, in the biometric signal acquisition device according to the present invention, the main body may be softly engaged with the fixing portion and the main body may be supported with an adequate force in a case where the main body is fixed to the body.

Further, the biometric signal acquisition device according to the present invention may maintain skin health and hygiene even during prolonged wearing.

The spirit of the present invention has been described only by way of example hereinabove, and the present invention may be variously modified, altered, and substituted by those skilled in the art to which the present invention pertains without departing from essential features of the present invention.

Accordingly, the exemplary embodiments disclosed in the present invention and the accompanying drawings do not limit but describe the spirit of the present invention, and the scope of the present invention is not limited by the exemplary embodiments and the accompanying drawings. The scope of the present invention should be interpreted by the following claims and it should be interpreted that all spirits equivalent to the following claims fall within the scope of the present invention.

What is claimed is:

1. A body-attachable biometric signal acquisition device comprising:
   a main body including a sensor acquiring a biometric signal in a state of closely adhering to a surface of a body; and
   a first fixing portion winding the body to fix the main body to the body,
   wherein the first fixing portion includes a first strap winding the body, the first strap including a framework formed of an elastic material,
   wherein, when the first strap winds the body to fasten the main body and the first fixing portion to the body, a pressure applied by the sensor to the surface of the body is generated by an elastic restoring moment generated by the framework, and
   wherein the framework comprises:
   a main body support portion formed to surround a side surface of the main body to support the main body when the main body is engaged with the first fixing portion; and
   elastic restoring moment generating portions attached to or formed integrally with the main body support portion and generating the elastic restoring moment,
   wherein the first strap includes two straps extending from opposite outer side surfaces of the main body support portion,
   wherein the first fixing portion includes at least one air cushion each having an opened or closed cavity therein,
   wherein the at least one air cushion each is formed on a surface of each of the two straps at a position adjacent to the main body when the first strap winds the body to fasten the main body and the first fixing portion to the body, the surface of each of the two straps being a surface facing the body,
   wherein the air cushion supports the surface of the body to prevent the main body from wobbling when the first strap winds the body to fasten the main body and the first fixing portion to the body,
   wherein each of the two straps includes the framework formed of the elastic material, and an outer cover enclosing the framework or part of the framework, or fused to the framework, and formed of a fabric material or an elastic material, wherein the air cushion is formed integrally with or attached to the framework, and a volume of the cavity in the air cushion is decreased as the pressure is increased, and wherein the air cushion includes at least one arc-shaped member including at least one first hole formed in a direction perpendicular to a direction in which the outer cover extends from each of the opposite outer side surfaces of the main body support portion.

2. The body-attachable biometric signal acquisition device of claim 1, wherein the elastic restoring moment generating portions extend from opposite outer side surfaces of the main body support portion, respectively, and are attached to or formed integrally with the opposite outer side surfaces, respectively, the elastic restoring moment generating portions each have a distal end separated from the surface of the body when the sensor is brought into contact with an attaching portion of the body, and the elastic restoring moment generating portions each have one end connected to the main body support portion, the one end having a cross section which is taken in a direction perpendicular to a length direction of the elastic restoring moment generating portion and of which a thickness and an area are larger than those of a cross section of the distal end.

3. The body-attachable biometric signal acquisition device of claim 2, wherein the main body support portion is separable from the main body, a second hole is formed in the main body support portion in a direction away from the surface of the body so that the main body is engageable with the main body support portion, the second hole has one opening facing the body and having an area larger than that of the other opening, and a groove to which the main body support portion is fixed is formed along the side surface of the main body.

4. The body-attachable biometric signal acquisition device of claim 3, further comprising: a ring fused to an inner surface of the second hole along the inner surface of the second hole, and formed of a material having a hardness higher than that of a material of the main body support portion.

5. The body-attachable biometric signal acquisition device of claim 3, wherein the sensor is formed on a bottom surface of the main body, and roundings are formed at corners of the main body and the main body support portion that face the body.

6. The body-attachable biometric signal acquisition device of claim 3, wherein the main body support portion includes a top cover supporting a top portion of the main body to prevent the main body from being separated from the main body support portion.

7. The body-attachable biometric signal acquisition device of claim 2, wherein the main body support portion is separable from the main body, a second hole is formed in the main body support portion in a direction away from the surface of the body so that the main body is engageable with the main body support portion, and a rugged portion supporting the pressure generated between the sensor and the surface of the body is formed on a surface of the second hole with which the main body is engaged.

8. The body-attachable biometric signal acquisition device of claim 7, wherein the rugged portion has a curved cross section.

9. The body-attachable biometric signal acquisition device of claim 8, wherein the rugged portion has an S-letter shaped cross section.

10. The body-attachable biometric signal acquisition device of claim 7, wherein the main body support portion includes a support supporting a bottom portion of the main body to prevent the main body from slipping on the surface of the body.

11. The body-attachable biometric signal acquisition device of claim 2, wherein the main body support portion has any one of a rectangular shape, a square shape, a circular shape, or an oval shape, when viewed from top direction from a side facing away from the body.

12. The body-attachable biometric signal acquisition device of claim 2, wherein an entire length of the framework is half or more than half of a circumference of a portion of the body on which the first fixing portion winds, the first fixing portion includes fasteners formed at opposite distal ends of the first fixing portion, respectively, and fastened to each other, and a fastening position or a fastening area of the fasteners is adjustable according to a size variation of the body.

13. The body-attachable biometric signal acquisition device of claim 1, wherein the elastic restoring moment generating portions extend from opposite outer side surfaces of the main body support portion, respectively, and are attached to or formed integrally with the opposite outer side surfaces, respectively, the elastic restoring moment generating portions each have a distal end separated from the surface of the body when the sensor is brought into contact with an attaching portion of the body, and the elastic restoring moment generating portion includes a first elastic material member connected to the main body support portion, and a second elastic material member fused to or adhering to the first elastic material member and having a hardness lower than that of the first elastic material member by a predetermined value.

14. The body-attachable biometric signal acquisition device of claim 1, wherein a number of the at least one first holes formed in the arc-shaped member is plural.

15. The body-attachable biometric signal acquisition device of claim 1, wherein the air cushion is formed of a fabric material and formed on a surface of the outer cover at a position adjacent to the main body, the surface of the outer cover being a surface facing the body when the first strap winds the body to fasten the main body and the first fixing portion to the body.

16. The body-attachable biometric signal acquisition device of claim 1, wherein the outer cover is fused to the elastic restoring moment generating portion and formed of an elastic material having a hardness lower than that of the elastic restoring moment generating portion, and the air cushion is formed on a surface of the outer cover at a position adjacent to the main body, the surface of the outer cover being a surface facing the body when the first strap winds the body to fasten the main body and the first fixing portion to the body.

17. The body-attachable biometric signal acquisition device of claim 1, wherein the outer cover is formed of the fabric material, is connected to the elastic restoring moment generating portion and the air cushion with a hook-and-loop fastener, and encloses the elastic restoring moment generating portion and the air cushion.

18. The body-attachable biometric signal acquisition device of claim 17, wherein opposite sides of the elastic restoring moment generating portion each have a ring shape with an empty middle portion, and the outer cover is sewed along an inner boundary of the ring shape.

19. The body-attachable biometric signal acquisition device of claim 17, wherein linings positioned at one surface of the outer cover, and outer shells positioned at another surface opposite to the one surface are formed of one or more layers of fabric material, the one surface facing the surface of the body when the first fixing portion winds the body to fasten the main body to the body, and
the elastic restoring moment generating portion adheres or is fused between the linings and the outer shells.

20. The body-attachable biometric signal acquisition device of claim 19, wherein the linings are formed of a material having a hardness lower than that of the outer shells,
the outer shells are formed of a material that is attachable with the hook-and-loop fastener, and
the linings and the outer shells adhere or are fused to the elastic restoring moment generating portion by using an adhesive, an adhesion film, or a synthetic resin material.

21. The body-attachable biometric signal acquisition device of claim 17, wherein the elastic restoring moment generating portion includes one or more sewing holes for sewing and is sewed to the outer cover through the sewing holes.

22. The body-attachable biometric signal acquisition device of claim 1, wherein the outer cover is fused to a surface or part of the surface of the elastic restoring moment generating portion, the surface being a surface facing the body when the first fixing portion winds the body to fasten the main body to the body,
the outer cover is formed of the elastic material having a hardness lower than that of the elastic restoring moment generating portion, and
the outer cover and the elastic restoring moment generating portion are fused to each other while forming an inclined surface at a predetermined angle.

23. The body-attachable biometric signal acquisition device of claim 22, wherein the outer cover and the elastic restoring moment generating portion are fused in a diagonal line shape, a V-letter shape, or a saw-tooth shape.

24. The body-attachable biometric signal acquisition device of claim 22, wherein the outer cover is further fused to a surface or part of the surface of the elastic restoring moment generating portion opposite to the surface facing the body.

25. The body-attachable biometric signal acquisition device of claim 1, wherein the framework comprises a plurality of sub-frameworks, and the sub-frameworks are formed to be spaced apart from opposite outer side surfaces of the main body by a predetermined distance, respectively, and extend from the opposite outer side surfaces of the main body, respectively.

26. The body-attachable biometric signal acquisition device of claim 25, wherein the sub-frameworks each have a distal end separated from the surface of the body when the sensor is brought into contact with an attaching portion of the body, and
the sub-frameworks each have one end connected to the main body support portion, the one end having a cross section which is taken in a direction perpendicular to a length direction of the sub-framework and of which a thickness and an area are larger than those of a cross section of the distal end.

27. The body-attachable biometric signal acquisition device of claim 26, wherein a protruding portion is formed at each of the opposite outer side surfaces of the main body, and a slot to which the first strap is detachably attached is formed at a distal end of the protruding portion.

28. The body-attachable biometric signal acquisition device of claim 26, further comprising outer covers each fused to a surface or part of the surface of the framework, the surface being opposite to a surface facing the body.

29. The body-attachable biometric signal acquisition device of claim 25, wherein the sub-frameworks each have a distal end separated from the surface of the body when the sensor is brought into contact with an attaching portion of the body, and
the sub-frameworks each include a first elastic material member, and a second elastic material member fused to a distal end of the first elastic material member in a length direction and having a hardness lower than that of the first elastic material member by a predetermined value.

30. A body-attachable biometric signal acquisition device comprising:
a main body including a sensor acquiring a biometric signal in a state of closely adhering to a surface of a body; and
a first fixing portion winding the body to fix the main body to the body,
wherein the first fixing portion includes a first strap winding the body, the first strap including a framework formed of an elastic material,
wherein, when the first strap winds the body to fasten the main body and the first fixing portion to the body, a pressure applied by the sensor to the surface of the body is generated by an elastic restoring moment generated by the framework, and
wherein the framework comprises:
a main body support portion formed to surround a side surface of the main body to support the main body when the main body is engaged with the first fixing portion; and
elastic restoring moment generating portions attached to or formed integrally with the main body support portion and generating the elastic restoring moment,
wherein the body-attachable biometric signal acquisition device further comprises air cushions each having a cavity therein or padded, and formed on end portions of the opposite outer side surfaces of the main body, the end portions facing the body,
wherein the air cushion supports the surface of the body to prevent the main body from wobbling when the first strap winds the body to fasten the main body and the first fixing portion to the body, and
the air cushion includes at least one arc-shaped member including at least one first hole formed in a direction perpendicular to a direction in which an outer cover extends from each of the opposite outer side surfaces of the main body support portion.

31. The body-attachable biometric signal acquisition device of claim 30, wherein the outer cover is formed of an elastic material having a hardness lower than that of the material of the framework,
wherein the outer cover is fused to a surface or part of the surface of the framework, the surface being a surface facing the body when the first fixing portion winds the body to fasten the main body to the body, and the outer cover encloses the framework, or the outer cover and the framework are fused to each other while forming an inclined surface at a predetermined angle.

32. The body-attachable biometric signal acquisition device of claim 31, wherein the outer cover and the framework are fused in a diagonal line shape, a V-letter shape, or a saw-tooth shape.

33. The body-attachable biometric signal acquisition device of claim 31, wherein the outer cover is further fused to a surface or part of the surface of the framework opposite to the surface facing the body.

34. A body-attachable biometric signal acquisition device comprising:
- a main body including a sensor acquiring a biometric signal in a state of closely adhering to a surface of a body; and
- a first fixing portion winding the body to fix the main body to the body,
- wherein the first fixing portion includes a first strap winding the body, the first strap including a framework formed of an elastic material,
- wherein, when the first strap winds the body to fasten the main body and the first fixing portion to the body, a pressure applied by the sensor to the surface of the body is generated by an elastic restoring moment generated by the framework, and
- wherein the framework comprises:
- a main body support portion formed to surround a side surface of the main body to support the main body when the main body is engaged with the first fixing portion; and
- elastic restoring moment generating portions attached to or formed integrally with the main body support portion and generating the elastic restoring moment,
- wherein the elastic restoring moment generating portions extend from opposite outer side surfaces of the main body support portion, respectively, and are attached to or formed integrally with the opposite outer side surfaces, respectively,
- the elastic restoring moment generating portions each have a distal end separated from the surface of the body when the sensor is brought into contact with an attaching portion of the body, and
- the elastic restoring moment generating portions each have one end connected to the main body support portion, the one end having a cross section which is taken in a direction perpendicular to a length direction of the elastic restoring moment generating portion and of which a thickness and an area are larger than those of a cross section of the distal end,
- wherein the main body support portion is separable from the main body,
- a hole is formed in the main body support portion in a direction away from the surface of the body so that the main body is engageable with the main body support portion,
- the hole has one opening facing the body and having an area larger than that of the other opening, and
- a groove to which the main body support portion is fixed is formed along the side surface of the main body, and
- wherein the body-attachable biometric signal acquisition device further comprises a ring fused to an inner surface of the hole along the inner surface of the hole, and formed of a material having a hardness higher than that of a material of the main body support portion.

* * * * *